(12) United States Patent
Yeaman

(10) Patent No.: US 10,543,250 B2
(45) Date of Patent: Jan. 28, 2020

(54) ANTIMICROBIAL FUSION PEPTIDES

(71) Applicant: Los Angeles Biomedical Research Institute at Harbor-UCLA Medical Center, Torrance, CA (US)

(72) Inventor: Michael R. Yeaman, Redondo Beach, CA (US)

(73) Assignee: Los Angeles Biomedical Research Institute at Harbor-UCLA Medical Center, Torrance, CA (US)

(*) Notice: Subject to any disclaimer, the term of this patent is extended or adjusted under 35 U.S.C. 154(b) by 140 days.

(21) Appl. No.: 15/579,926

(22) PCT Filed: Jun. 3, 2016

(86) PCT No.: PCT/US2016/035896
§ 371 (c)(1),
(2) Date: Jul. 2, 2018

(87) PCT Pub. No.: WO2016/197049
PCT Pub. Date: Dec. 8, 2016

(65) Prior Publication Data
US 2018/0221439 A1 Aug. 9, 2018

Related U.S. Application Data

(60) Provisional application No. 62/171,868, filed on Jun. 5, 2015.

(51) Int. Cl.
| | | |
|---|---|---|
| *A61K 38/16* | (2006.01) | |
| *C07K 14/195* | (2006.01) | |
| *A61P 33/06* | (2006.01) | |
| *A61P 31/04* | (2006.01) | |
| *A61K 9/00* | (2006.01) | |
| *A61K 38/00* | (2006.01) | |
| *A61K 31/407* | (2006.01) | |
| *A61K 31/542* | (2006.01) | |
| *A61K 38/12* | (2006.01) | |
| *A61K 31/351* | (2006.01) | |
| *A61K 31/365* | (2006.01) | |
| *A61K 31/4418* | (2006.01) | |

(52) U.S. Cl.
CPC .......... *A61K 38/16* (2013.01); *A61K 9/0019* (2013.01); *A61P 31/04* (2018.01); *A61P 33/06* (2018.01); *A61K 31/351* (2013.01); *A61K 31/365* (2013.01); *A61K 31/407* (2013.01); *A61K 31/4418* (2013.01); *A61K 31/542* (2013.01); *A61K 38/12* (2013.01); *A61K 2300/00* (2013.01)

(58) Field of Classification Search
CPC .......... A61K 2300/00; A61K 31/351; A61K 31/365; A61K 31/407; A61K 31/4418; A61K 31/542; A61K 38/00; A61K 38/12; A61K 38/16; A61K 9/0019; A61P 31/04; A61P 33/06; C07K 14/195; Y02A 50/411
See application file for complete search history.

(56) References Cited

U.S. PATENT DOCUMENTS

| | | | | |
|---|---|---|---|---|
| 7,820,619 B1 * | 10/2010 | Yeaman | ............... | C07K 7/06 514/2.3 |
| 2008/0170991 A1 | 7/2008 | Shi et al. | | |
| 2011/0319319 A1 | 12/2011 | Yount et al. | | |
| 2012/0232012 A1 | 9/2012 | Popel et al. | | |
| 2014/0296137 A1 | 10/2014 | Rajamani et al. | | |

FOREIGN PATENT DOCUMENTS

WO    WO2007149542    * 12/2007    ............. C07K 14/43

OTHER PUBLICATIONS

Chen et al. Fusion protein linkers: Property, design and functionality. Advanced Drug Delivery Reviews. vol. 65, pp. 1357-1369. (Year: 2013).*
Erfe et al., "Efficacy of Synthetic Peptides RP-1 and AA-RP-1 against *Leishmania* Species In Vitro and In Vivo", Antimicrobial Agents and Chemotherapy (2011), pp. 658-665.
Extended European Search Report of EP 16804596 dated Nov. 26, 2018 (10 pages).
Michael Yeaman, "Efficacy of Intravenous Kinocidin gamma-RP-1 versus Multi-Drug-Resistant Acinetobacter baumanniiPneumonia in a Neutropenic Murine Model (Poster #72-MHSRS-687)", Military Health System Research Symposium, Aug. 21, 2014 (p. 44.
Yeaman et al., "Modular determinants of antimicrobial activity in platelet factor-4 family kinocidins", Biochimica et Biophysica Acta 1768 (2007) pp. 609-619.
Yeaman et al., "Synthetic Peptides That Exert Antimicrobial Activities in Whole Blood and Blood-Derived Matrices", Antimicrobial Agents and Chemotherapy, vol. 46, No. 12, Dec. 2002, pp. 3883-3891.
Yeaman, "Platelets: at the nexus of antimicrobial defence", Macmillan Publisher Limited, Jun. 2014, vol. 12, pp. 426-437.
Yount et al., "Peptide antimicrobials: cell wall as a bacterial target", Annals of the New York Academy of Sciences 1277 (2013) pp. 127-138.
Yount et al., "Platelet Microbicidal Protein 1: Structural Themes of a Multifunctional Antimicrobial Peptide", Antimicrobial Agents and Chemotherapy, vol. 48, No. 11, Nov. 2004, pp. 4395-4404.
Yount et al., "Structural correlates of antimicrobial efficacy in IL-8 and related human kinocidins", Biochimica et Biophysica Acta 1768 (2007) pp. 598-608.

* cited by examiner

*Primary Examiner* — Marcela M Cordero Garcia
(74) *Attorney, Agent, or Firm* — Sheppard Mullin Richter & Hampton LLP

(57) ABSTRACT

Antimicrobial peptides, compositions and methods are described that are useful for treating infectious diseases, including those caused by drug resistant Gram-negative bacteria (e.g., *Pseudomonas* and *Acinetobacter*) and parasite-caused diseases such as malaria. The peptides include a modular kinocidin gamma-core connected directly, or through a short spacer, to a kinocidin C-terminal alpha-helix.

20 Claims, 19 Drawing Sheets

Specification includes a Sequence Listing.

| MDRAB Strain | RP-1 | γ-RP-1 | CEF | COL | IMI |
|---|---|---|---|---|---|
| 19606 | 100 | 12.5 | 8 | 8 | <0.5 |
| 17978 | 25 | 50 | 4 | 16 | <0.5 |
| 23055 | 6.25 | 25 | <0.5 | 8 | <0.5 |
| 17906 | 6.25 | 50 | 2 | 32 | <0.5 |
| 17925 | 6.25 | 25 | 1 | 8 | <0.5 |

MIC (CLSI) — Antimicrobial Agent

```
                        SEQUENCE LISTING

<160> NUMBER OF SEQ ID NOS: 17

<210> SEQ ID NO 1
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Cys Pro Thr Ala Gln Leu Ile Ala Thr Leu Lys Asn Gly Arg Lys Ile
1               5                   10                  15

Cys Leu Asp Leu Gln Ala Leu Tyr Lys Lys Phe Lys Lys Lys Leu Leu
            20                  25                  30

Lys Ser Leu Lys Arg Leu Gly
        35

<210> SEQ ID NO 2
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Cys Pro Thr Ala Gln Leu Ile Ala Thr Leu Lys Asn Gly Arg Lys Ile
1               5                   10                  15

Cys Leu Asp Leu Gln
            20

<210> SEQ ID NO 3
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Ala Leu Tyr Lys Lys Phe Lys Lys Lys Leu Leu Lys Ser Leu Lys Arg
1               5                   10                  15

Leu Gly

<210> SEQ ID NO 4
<211> LENGTH: 22
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 4

Cys Pro Thr Ala Gln Leu Ile Ala Thr Leu Lys Asn Gly Arg Lys Ile
1               5                   10                  15

Cys Leu Asp Leu Gln Pro
            20

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Cys Pro Thr Ala Gln Leu Ile Ala Thr Leu Lys Asn Gly Arg Lys Ile
1               5                   10                  15

Cys Leu Asp Leu Gln Ala Pro
            20

<210> SEQ ID NO 6
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Cys Pro Thr Ala Gln Leu Ile Ala Thr Leu Lys Asn Gly Pro Lys Ile
1               5                   10                  15

Cys Leu Asp Leu Gln
            20

<210> SEQ ID NO 7
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Pro Thr Ala Gln Leu Ile Ala Thr Leu Lys Asn Gly Arg Lys Ile
1               5                   10                  15

Cys Leu Asp Leu Gln Ala
            20

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Cys Pro Thr Ala Gln Leu Ile Ala Thr Leu Lys Asn Gly Arg Lys Ile
1               5                   10                  15

Pro Leu Asp Leu Gln
            20
```

```
<210> SEQ ID NO 9
<211> LENGTH: 19
<212> TYPE: PRT
<213> ORGANISM: Homo sapiens

<400> SEQUENCE: 9

Lys Glu Asn Trp Val Gln Arg Val Val Glu Lys Phe Leu Lys Arg Ala
1               5                   10                  15

Glu Asn Ser

<210> SEQ ID NO 10
<211> LENGTH: 38
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 10

Ala Asn Thr Glu Ile Ile Val Lys Leu Ser Asp Gly Arg Glu Leu Cys
1               5                   10                  15

Leu Asp Pro Lys Glu Asn Trp Val Gln Arg Val Val Glu Lys Phe Leu
            20                  25                  30

Lys Arg Ala Glu Asn Ser
        35

<210> SEQ ID NO 11
<211> LENGTH: 32
<212> TYPE: PRT
<213> ORGANISM: Unknown
<220> FEATURE:
<223> OTHER INFORMATION: Description of Unknown: Rabbit polypeptide

<400> SEQUENCE: 11

Asn Leu Ile Ala Thr Lys Lys Asn Gly Arg Lys Leu Cys Leu Asp Leu
1               5                   10                  15

Gln Ala Ala Leu Tyr Lys Lys Ile Ile Lys Lys Leu Leu Glu Ser
            20                  25                  30

<210> SEQ ID NO 12
<211> LENGTH: 19
<212> TYPE: PRT
<213> ORGANISM: Homo sapiens

<400> SEQUENCE: 12

Ala Asn Thr Glu Ile Ile Val Lys Leu Ser Asp Gly Arg Glu Leu Cys
1               5                   10                  15

Leu Asp Pro

<210> SEQ ID NO 13
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Cys Pro Thr Ala Gln Leu Ile Ala Thr Leu Lys Asn Gly Arg Lys Ile
1               5                   10                  15

Cys Leu Asp Leu Gln Ala Ala Leu Tyr Lys Lys Phe Lys Lys Lys Leu
            20                  25                  30
```

Leu Lys Ser Leu Lys Arg Leu Gly
        35                  40

<210> SEQ ID NO 14
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Cys Pro Thr Ala Gln Leu Ile Ala Thr Leu Lys Asn Gly Arg Lys Ile
1               5                   10                  15

Cys Leu Asp Leu Gln Pro Ala Leu Tyr Lys Lys Phe Lys Lys Lys Leu
            20                  25                  30

Leu Lys Ser Leu Lys Arg Leu Gly
        35                  40

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Cys Pro Thr Ala Gln Leu Ile Ala Thr Leu Lys Asn Gly Arg Lys Ile
1               5                   10                  15

Pro Leu Asp Leu Gln Ala Leu Tyr Lys Lys Phe Lys Lys Lys Leu Leu
            20                  25                  30

Lys Ser Leu Lys Arg Leu Gly
        35

<210> SEQ ID NO 16
<211> LENGTH: 41
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Cys Pro Thr Ala Gln Leu Ile Ala Thr Leu Lys Asn Gly Arg Lys Ile
1               5                   10                  15

Cys Leu Asp Leu Gln Ala Pro Ala Leu Tyr Lys Lys Phe Lys Lys Lys
            20                  25                  30

Leu Leu Lys Ser Leu Lys Arg Leu Gly
        35                  40

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

-continued

```
Cys Pro Thr Ala Gln Leu Ile Ala Thr Leu Lys Asn Gly Pro Lys Ile
1               5                   10                  15

Cys Leu Asp Leu Gln Ala Leu Tyr Lys Lys Phe Lys Lys Lys Leu Leu
            20                  25                  30

Lys Ser Leu Lys Arg Leu Gly
        35
```

ANTIMICROBIAL FUSION PEPTIDES

CROSS-REFERENCE TO RELATED APPLICATIONS

This application is a U.S. National Stage Application under 35 U.S.C. § 371 of International Application No. PCT/US2016/035896, filed Jun. 3, 2016, which claims the benefit under 35 U.S.C. § 119(e) to U.S. Provisional Application Ser. No. 62/171,868, filed on Jun. 5, 2015, each of which is hereby incorporated by reference in its entirety.

SEQUENCE LISTING

The instant application contains a Sequence Listing which has been submitted in ASCII format via EFS-Web and is hereby incorporated by reference in its entirety. Said ASCII copy, created on Jun. 29, 2018, is named 213137-US_ST25.txt and is 8,192 bytes in size.

BACKGROUND

Infection is an increasingly serious problem to public health, from intensive care units (ICUs), to trauma and wound infection, to infections among the immune compromised. Infection is associated with unacceptable morbidity, mortality, and cost. According to the results of the recent EPIC II studies, infected patients have much higher hospital mortality rates, up to 33.1% versus 14.8% for non-infected patients. Despite the recent media attention focused on methicillin-resistant *Staphylococcus aureus* (MRSA), the looming threat in MDR pathogens over the last decade has increasingly been the rise of Gram-negative pathogens *Pseudomonas aeurginosa* (PA) or *Acinetobacter baumannii* (AB).

Such pathogens are isolated in 62% of patients in ICU settings, versus 47% for Gram-positive pathogens. *Pseudomonas aeruginosa* is one of the most common life-threatening pathogens in public health, particularly among immune compromised or immune suppressed patients. Infections caused by multi-drug-resistant *Pseudomonas aeurginosa* (MDRPA) can occur in any person, including hospital acquired pneumonia, catheter-associated infections and bacteremia, sepsis, respiratory infections, penetrating, crushing, or wound infections, and community-acquired infections of the eyes, ears, or sinuses from waterborne sources. Recent, population-based data of nosocomial infections caused by MDRPA in Europe identified an incidence of 126 cases per 100,000 individuals.

Likewise, multi-drug-resistant *Acinetobacter baumannii* (MDRAB) is an increasingly urgent and unaddressed pathogen responsible for life-threatening infections, particularly in ICU settings, including ventilator associated pneumonia, bacteremia, surgical site infection, and sepsis. Treating such infections caused by MDRAB is difficult due to resistance to multiple antibiotics, including carbapenems, and attributable mortality rates are high.

Infections caused by MDRPA and MDRAB are virtually always resistant to many classes of antibiotics, and commonly resistant all antibiotics in the medical formulary. Thus, there are increasing reports of truly pan-resistant infections due to these organisms which cannot be treated with any available antibiotic or combination.

Correlating with a highly antibiotic-resistant nature, infections caused by MDRPA or MDRAB are associated with high mortality rates. For example, MDRPA is associated with increased risk of mortality from sepsis, and is a significant predictor of ICU mortality. Finally, there is a concerning absence of new antibiotics or those in development that have novel mechanisms of action against these agents. For example, even a recently approved antibiotic, tigecycline, is inactive vs. MDRPA. Of greater concern, few if any antibiotics currently in phase II or later clinical trials has improved efficacy against MDRPA or MDRAB as compared with existing agents. These alarming trends underscore the desperate need for new strategies to treat antibiotic-resistant and deadly Gram-negative infections.

Another wide-spread infectious disease is malaria. Uncomplicated malaria may be treated with oral medications. The current treatment for *P. falciparum* infection is the use of artemisinins in combination with other antimalarials (known as artemisinin-combination therapy, or ACT), which may decrease resistance to any single drug component. These additional antimalarials include: amodiaquine, lumefantrine, mefloquine or sulfadoxine/pyrimethamine. Another recommended combination is dihydroartemisinin and piperaquine. ACT is about 90% effective when used to treat uncomplicated malaria. Infection with *P. vivax, P. ovale* or *P. malariae* is usually treated without the need for hospitalization. Treatment of *P. vivax* requires both treatment of blood stages (with chloroquine or ACT) and clearance of liver forms with primaquine. Recommended treatment for severe malaria is the intravenous use of antimalarial drugs. For severe malaria, artesunate is superior to quinine in both children and adults.

Despite potential benefits of combination therapy, drug resistance to various malaria treatments poses a growing problem in the 21st-century. Resistance is now common against all classes of antimalarial drugs apart from artemisinins. Treatment of resistant strains became increasingly dependent on this class of drugs. The cost of artemisinins limits their use in the developing world. Malaria strains found on the Cambodia-Thailand border are resistant to combination therapies that include artemisinins, and may therefore be untreatable. Exposure of the parasite population to artemisinin monotherapies in subtherapeutic doses for over 30 years and the availability of substandard artemisinins likely drove the selection of the resistant phenotype.

SUMMARY

The present disclosure describes antimicrobial peptides, compositions and methods that are useful for treating infectious diseases, in particular those caused by drug resistant Gram-negative bacteria (e.g., *Pseudomonas* and *Acinetobacter*) and parasite-caused diseases such as malaria. Such antimicrobial peptides, compositions and methods are also suitable for treating fungus or virus-caused infections, without limitation. In some embodiments, the peptides include a modular kinocidin gamma-core connected directly, or through a short spacer, to a kinocidin C-terminal alpha-helix.

In one embodiment, the present disclosure provides an isolated peptide comprising (1) a first fragment consisting of the amino acid sequence of SEQ ID NO:2 (CPTAQLI-ATLKNGRKICLDLQ) or a first amino acid sequence having at least 85% sequence identity to SEQ ID NO: 2; and (2) a second fragment consisting of the amino acid sequence of SEQ ID NO:3 (ALYKKFKKKLLKSLKRLG) or a second amino acid sequence having at least 85% sequence identity to SEQ ID NO: 3, wherein the first fragment and the second fragment are connected directly or connected through a spacer that is 10 amino acids or fewer in length.

In some aspects, the first fragment is at the N-terminal end of the second fragment. In some aspects, the first fragment and the second fragment are connected directly. In some aspects, the first fragment and the second fragment are connected through the spacer. In some aspects, the spacer is 5 amino acids or fewer in length. In some aspects, the spacer comprises one or more glycine.

In some aspects, the first fragment consists of the amino acid sequence of SEQ ID NO:4 (CPTAQLIATLKNGRKICLDLQP). In some aspects, the first fragment consists of the amino acid sequence of SEQ ID NO:5 (CPTAQLIATLKNGRKICLDLQAP). In some aspects, the first fragment consists of the amino acid sequence of SEQ ID NO:6 (CPTAQLIATLKNGPKICLDLQ).

In some aspects, the peptide comprises the amino acid sequence of SEQ ID NO:1 (CPTAQLIATLKNGRKICLDLQALYKKFKKKLLKSLKRLG). In some aspects, the peptide comprises the amino acid sequence of SEQ ID NO:13 (CPTAQLIATLKNGRKICLDLQAALYKKFKKKLLKSLKRLG). In some aspects, the peptide comprises the amino acid sequence of SEQ ID NO:14 (CPTAQLIATLKNGRKICLDLQPALYKKFKKKLLKSLKRLG). In some aspects, the peptide comprises the amino acid sequence of SEQ ID NO:15 (CPTAQLIATLKNGRKIPLDLQALYKFKKKLLKSLKRLG).

In some aspects, the peptide is not longer than 100 amino acids in length. In some aspects, the peptide is not longer than 75 amino acids in length. In some aspects, the peptide is not longer than 50 amino acids in length. In some aspects, the peptide has antimicrobial activity.

In one embodiment, provided is a polynucleotide comprising a nuclei acid sequence encoding the peptide of any one of the peptides of the present disclosure. In another embodiment, provided is a composition comprising a peptide of the present disclosure and a pharmaceutically acceptable carrier. In some aspects, the composition further comprises an antimicrobial agent. In some aspects, the antimicrobial agent is selected from the group consisting of imipenem, ceftazidime, colistin, chloroquine, artemisinin, vancomycin and daptomycin.

Yet another embodiment provides a method of treating an infection in a patient in need thereof, comprising administering to the patient an effective amount of the peptide or composition of the present disclosure. In some aspects, the infection is caused by a Gram-negative bacterium. In some aspects, the infection is multi-drug-resistant. In some aspects, the infection is caused by multidrug-resistant *Pseudomonas aeruginosa* (MDRPA) or multidrug-resistant *Acinetobacter baumannii* (MDRAB).

In some aspects, the patient suffers from a disease or condition selected from the group consisting of wound abscess, catheter biofilm, pneumonia, and bacteremia. In some aspects, the infection is caused by a parasite. In some aspects, the patient suffers from malaria. In some aspects, the administration is intravenous or topical.

DETAILED DESCRIPTION

Figure 1A:
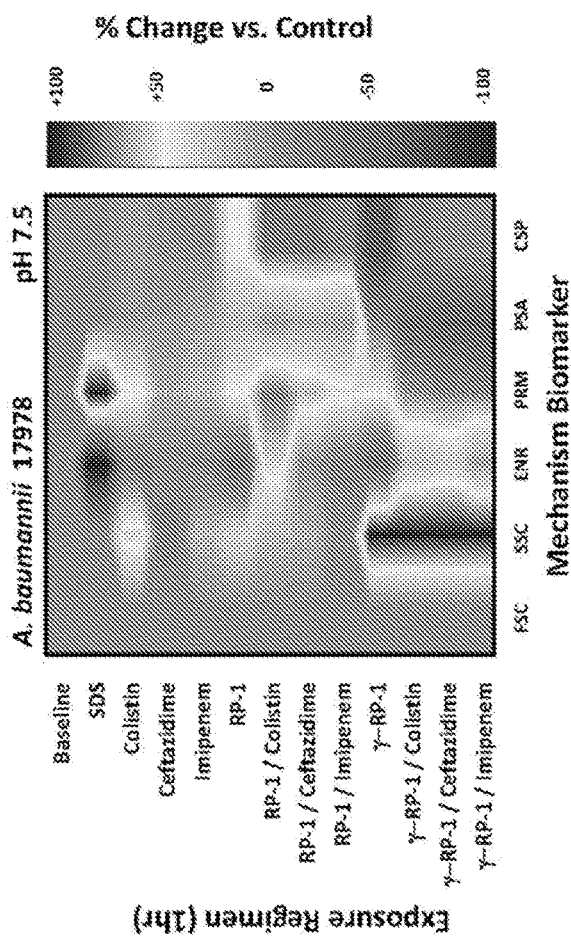
FIG. 1A-B illustrate RP-1 and γ-RP-1 composite mechanisms of action against MDRPA and MDRAB in vitro.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

It must be noted that as used herein and in the appended claims, the singular forms "a", "an", and "the" include plural referents unless the context clearly dictates otherwise. Thus, for example, reference to "a peptide" includes a plurality of peptides.

1. Definitions

Unless defined otherwise, all technical and scientific terms used herein have the same meaning as commonly understood by one of ordinary skill in the art to which this disclosure belongs. As used herein the following terms have the following meanings.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "sequence identity" refers to a level of amino acid residue or nucleotide identity between two peptides or between two nucleic acid molecules. When a position in the compared sequence is occupied by the same base or amino acid, then the molecules are identical at that position. A peptide (or a polypeptide or peptide region) has a certain percentage (for example, at least about 60%, or at least about 65%, or at least about 70%, or at least about 75%, or at least about 80%, or at least about 83%, or at least about 85%, or at least about 90%, or at least about 95%, or at least about 98% or at least about 99%) of "sequence identity" to another sequence means that, when aligned, that percentage of bases (or amino acids) are the same in comparing the two sequences. It is noted that, for any sequence ("reference sequence") disclosed in this application, sequences having at least about 60%, or at least about 65%, or at least about 70%, or at least about 75%, or at least about 80%, or at least about 83%, or at least about 85%, or at least about 90%, or at least about 95%, or at least about 98% or at least about 99% sequence identity to the reference sequence are also within the disclosure.

Likewise, the present disclosure also includes sequences that have one, two, three, four, or five substitution, deletion or addition of amino acid residues or nucleotides as compared to the reference sequences.

In any of the embodiments described herein, analogs of a peptide comprising any amino acid sequence described herein are also provided, which have at least about 80%, or at least about 83%, or at least about 85%, or at least about 90%, or at least about 95%, or at least about 98%, or at least about 99% sequence identity to any of reference amino acid sequences. In some embodiments, the analogs include one, two, three, four, or five substitution, deletion or addition of amino acid residues as compared to the reference sequences. In some embodiments, the substitution is a conservative substitution.

alanine, or the like. "Positively charged residues" relate to lysine, arginine, ornithine, or histidine. "Negatively charged residues" refer to aspartic acid or glutamic acid. Residues having "bulky side chains" refer to phenylalanine, tryptophan or tyrosine, or the like. A list of illustrative conservative amino acid substitutions is given in Table A.

TABLE A

| For Amino Acid | Replace With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

Alternatively, non-limiting examples of conservative amino acid substitutions are provided in the table below, where a similarity score of 0 or higher indicates conservative substitution between the two amino acids.

|   | C | G | P | S | A | T | D | E | N | Q | H | K | R | V | M | I | L | F | Y | W |
| --- | --- | --- | --- | --- | --- | --- | --- | --- | --- | --- | --- | --- | --- | --- | --- | --- | --- | --- | --- | --- |
| W | −8 | −7 | −6 | −2 | −6 | −5 | −7 | −7 | −4 | −5 | −3 | −3 | 2 | −6 | −4 | −5 | −2 | 0 | 0 | 17 |
| Y | 0 | −5 | −5 | −3 | −4 | −3 | −4 | −4 | −2 | −4 | 0 | −4 | −5 | −2 | −2 | −1 | −1 | 7 | 10 | |
| F | −4 | −5 | −5 | −3 | −4 | −3 | −6 | −5 | −4 | −5 | −2 | −5 | −4 | −1 | 0 | 1 | 2 | 9 | | |
| L | −6 | −4 | −3 | −3 | −2 | −2 | −4 | −3 | −3 | −2 | −2 | −3 | −3 | 2 | 4 | 2 | 6 | | | |
| I | −2 | −3 | −2 | −1 | −1 | 0 | −2 | −2 | −2 | −2 | −2 | −2 | −2 | 4 | 2 | 5 | | | | |
| M | −5 | −3 | −2 | −2 | −1 | −1 | −3 | −2 | 0 | −1 | −2 | 0 | 0 | 2 | 6 | | | | | |
| V | −2 | −1 | −1 | −1 | 0 | 0 | −2 | −2 | −2 | −2 | −2 | −2 | −2 | 4 | | | | | | |
| R | −4 | −3 | 0 | 0 | −2 | −1 | −1 | −1 | 0 | 1 | 2 | 3 | 6 | | | | | | | |
| K | −5 | −2 | −1 | 0 | −1 | 0 | 0 | 0 | 1 | 1 | 0 | 5 | | | | | | | | |
| H | −3 | −2 | 0 | −1 | −1 | −1 | 1 | 1 | 2 | 3 | 6 | | | | | | | | | |
| Q | −5 | −1 | 0 | −1 | 0 | −1 | 2 | 2 | 1 | 4 | | | | | | | | | | |
| N | −4 | 0 | −1 | 1 | 0 | 0 | 2 | 1 | 2 | | | | | | | | | | | |
| E | −5 | 0 | −1 | 0 | 0 | 0 | 3 | 4 | | | | | | | | | | | | |
| D | −5 | 1 | −1 | 0 | 0 | 0 | 4 | | | | | | | | | | | | | |
| T | −2 | 0 | 0 | 1 | 1 | 3 | | | | | | | | | | | | | | |
| A | −2 | 1 | 1 | 1 | 2 | | | | | | | | | | | | | | | |
| S | 0 | 1 | 1 | 1 | | | | | | | | | | | | | | | | |
| P | −3 | −1 | 6 | | | | | | | | | | | | | | | | | |
| G | −3 | 5 | | | | | | | | | | | | | | | | | | |
| C | 12 | | | | | | | | | | | | | | | | | | | |

As is well-known in the art, a "conservative substitution" of an amino acid or a "conservative substitution variant" of a peptide refers to an amino acid substitution which maintains: 1) the secondary structure of the peptide; 2) the charge or hydrophobicity of the amino acid; and 3) the bulkiness of the side chain or any one or more of these characteristics. Illustratively, the well-known terminologies "hydrophilic residues" relate to serine or threonine. "Hydrophobic residues" refer to leucine, isoleucine, phenylalanine, valine or As used herein, the term "composition" refers to a preparation suitable for administration to an intended patient for therapeutic purposes that contains at least one pharmaceutically active ingredient, including any solid form thereof. The composition may include at least one pharmaceutically acceptable component to provide an improved formulation of the compound, such as a suitable carrier. In certain embodiments, the composition is formulated as a film, gel, patch, or liquid solution.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

2. Antimicrobial Peptides

Meritorious efforts to translate antimicrobial activity of classical antimicrobial peptides (e.g., magainins or defensins) into novel systemic anti-infectives have met with considerable difficulty over the past decade. The predominant barriers yet to be overcome are toxicity and durable efficacy in the bloodstream. The activity of these antimicrobial peptides is typically restricted to phagolysosomes or to relatively inert epithelial surfaces, such as skin or mucosa. Beyond these contexts, such peptides are typically toxic, inactive, or degraded.

Kinocidins are naturally liberated into the bloodstream to exert their antimicrobial effects in the context of blood, plasma and serum. The C-terminal α-helix of kinocidins, when isolated, possess anti-infective activities that are similar to or even stronger than the natural kinocidins. RP-1 (ALYKKFKKKLLKSLKRLG; SEQ ID NO:3) is a consensus sequence obtained from the α-helix motifs of multiple kinocidin proteins. As shown in the experiments, RP-1 has antimicrobial activity against a wide range of human pathogens.

Another common structural element of the kinocidins is a multidimensional γ-core signature (see, e.g., Yount and Yeaman, *Proc Natl Acad Sci USA*. 101:7363-8, 2004). There was no report concerning the antimicrobial activity of the γ-core. Surprisingly, however, the present experimental examples demonstrate that γ-RP-1 (SEQ ID NO: 1), which fuses the RP-1 peptide to a γ-core of the CXCL4 protein, exhibited potent antimicrobial activities against a wide range of human pathogens, including Gram-negative bacteria and parasites. Even more surprisingly, γ-RP-1 is more potent than RP-1 and other comparative antimicrobial peptides, and is efficacious among a wider range of microorganisms, can exhibit activities in a wider variety of environments, and appears to have therapeutic tolerability. Importantly, the γ-RP-1 molecule exhibits greater efficacy against microbial pathogens in human blood than RP-1.

In accordance with one embodiment of the present disclosure, provided is a fusion peptide that includes RP-1 (SEQ ID NO: 3) or a variant thereof and the γ-core of CXCL4 (CPTAQLIATLKNGRKICLDLQ, SEQ ID NO: 2) or a variant thereof.

A variant of RP-1, as used herein, refers to a peptide that has a certain level of sequence identity to RP-1, or a peptide that can be made by modifying the RP-1 peptide with one, two or three amino acid addition, deletion and/or substitution (e.g., conservative substitutions as illustrated in Table A). The level of sequence identity, in one aspect, is at least about 80%. In another aspect, the level of sequence identify is at least about 85%, at least about 90%, or at least about 95%.

A variant of CXCL4 γ-core (SEQ ID NO: 2), as used herein, refers to a peptide that has a certain level of sequence identity to the γ-core, or a peptide that can be made by modifying the γ-core with one, two or three amino acid addition, deletion and/or substitution (e.g., conservative substitutions as illustrated in Table A). The level of sequence identity, in one aspect, is at least about 80%. In another aspect, the level of sequence identify is at least about 85%, at least about 90%, or at least about 95%.

In one aspect, addition of one, two or three amino acids can be at the N- or C-terminal end of the peptide. For instance, variants of the γ-core can include CPTAQLIATLKNGRKICLDLQP (SEQ ID NO: 4), CPTAQLIATLKNGRKICLDLQAP (SEQ ID NO: 5) and CPTAQLIATLKNGRKICLDLQA (SEQ ID NO: 7).

Addition, deletion or substitution does not need to be at the end of the peptide, however. For instance, even though Cys1 and Cys17 of SEQ ID NO: 2 form a disulfide bridge, substitution of Cys17 with a proline (i.e., CPTAQLIATLKNGRKIPLDLQ; SEQ ID NO: 8) did not impact the activity of the fusion peptide. Likewise, CPTAQLIATLKNGPKICLDLQ (SEQ ID NO: 6) is also a suitable variant of the γ-core.

A linker can optionally be included between the γ-core and RP-1, which is preferably 10 amino acids or fewer in length. In some aspects, the spacer is 9, 8, 6, 5, 4, 3, 2 amino acids in length or shorter. The spacer can include any amino acids, such as Ala, Pro, Cys, and Gly.

It is contemplated that the γ-core and RP-1 within the fusion peptide can be at either orientation, i.e., the RP-1 fragment can be at the N- or C-terminal end of the γ-core. The total length of the fusion peptide is preferably not longer than 100 amino acids in length, and more preferably not longer than 90, 85, 80, 75, 70, 65, 60, 55, or 50 amino acids in length.

In some embodiments, the fusion peptide has antimicrobial activity.

In some embodiments, the peptides of the present disclosure include SEQ ID NO:1 and peptides that are modified from SEQ ID NO:1 by including one, two or three substitution, insertion/addition, deletion, or the combination therefore. In one aspect, the insertion is with amino acid residues with small side chains such as glycine. In one aspect, at least one insertion is between amino acids 20 and 21, between amino acids 21 and 22, or between amino acids 22 and 23. In one aspect, such insertion at a particular location is one, two or three amino acids.

In some embodiments, the peptides of the present disclosure are at least 35 amino acid in length, or alternatively at least 36, 37, 38, 39, 40, 41, 42, 43, 44, 45, 46, 47, 48, 49, 50, 51, 52, 53, 54, 55, 56, 57, 58, 59, 60, 65, 70, 75, or 80 amino acids. In some embodiments, the peptides of the present disclosure are not longer than 80 amino acids, or not longer than 75, 70, 65, 60, 59, 58, 57, 56, 55, 54, 53, 52, 51, 50, 49, 48, 47, 46, 45, 44, 43, 42, 41, or 40 amino acids.

In some embodiments, the peptides may be conjugated to therapeutic agents, prodrugs, peptides, proteins, enzymes, viruses, lipids, biological response modifiers, pharmaceutical agents, or PEG.

The peptides may be conjugated or fused to a therapeutic agent, which may include detectable labels such as radioactive labels, an immunomodulator, a hormone, an enzyme, an oligonucleotide, a photoactive therapeutic or diagnostic agent, a cytotoxic agent, which may be a drug or a toxin, an ultrasound enhancing agent, a non-radioactive label, a combination thereof and other such agents known in the art. The peptides can be detectably labeled by coupling it to a chemiluminescent compound. The presence of the chemiluminescent-tagged antigen-binding polypeptide is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

3. Synthesis of Antimicrobial Peptides

The peptides described herein can be ordered from a commercial source or partially or fully synthesized using methods well known in the art (e.g., chemical and/or biotechnological methods). In certain embodiments, the peptides are synthesized according to solid phase peptide synthesis protocols that are well known in the art. In another embodiment, the peptide is synthesized on a solid support according to the well-known Fmoc protocol, cleaved from the support with trifluoroacetic acid and purified by chromatography according to methods known to persons skilled in the art. In other embodiments, the peptide is synthesized utilizing the methods of biotechnology that are well known to persons skilled in the art. In one embodiment, a DNA sequence that encodes the amino acid sequence information for the desired peptide is ligated by recombinant DNA techniques known to persons skilled in the art into an expression plasmid (for example, a plasmid that incorporates an affinity tag for affinity purification of the peptide), the plasmid is transfected into a host organism for expression, and the peptide is then isolated from the host organism or the growth medium, e.g., by affinity purification.

The peptides can be also prepared by using recombinant expression systems. Generally, this involves inserting the nucleic acid molecule into an expression system to which the molecule is heterologous (i.e., not normally present). One or more desired nucleic acid molecules encoding a peptide of the disclosure may be inserted into the vector. When multiple nucleic acid molecules are inserted, the multiple nucleic acid molecules may encode the same or different peptides. The heterologous nucleic acid molecule is inserted into the expression system or vector in proper sense (5'→3') orientation relative to the promoter and any other 5' regulatory molecules, and correct reading frame.

Purified peptides may be obtained by several methods. The peptide is preferably produced in purified form (preferably at least about 80% or 85% pure, more preferably at least about 90% or 95% pure) by conventional techniques. Depending on whether the recombinant host cell is made to secrete the peptide into growth medium (see U.S. Pat. No. 6,596,509 to Bauer et al., which is hereby incorporated by reference in its entirety), the peptide can be isolated and purified by centrifugation (to separate cellular components from supernatant containing the secreted peptide) followed by sequential ammonium sulfate precipitation of the supernatant. The fraction containing the peptide is subjected to gel filtration in an appropriately sized dextran or polyacrylamide column to separate the peptides from other proteins. If necessary, the peptide fraction may be further purified by HPLC.

4. Antimicrobial Compositions and Formulations

Compositions and formulations that include any one or more of the peptides as disclosed herein are also provided. In one embodiment, the composition includes any one or more of the peptides and a pharmaceutically acceptable carrier.

"Pharmaceutically acceptable carriers" refers to any diluents, excipients, or carriers that may be used in the compositions of the disclosure. Pharmaceutically acceptable carriers include ion exchangers, alumina, aluminum stearate, lecithin, serum proteins, such as human serum albumin, buffer substances, such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Suitable pharmaceutical carriers are described in Remington's Pharmaceutical Sciences, Mack Publishing Company, a standard reference text in this field. They are preferably selected with respect to the intended form of administration, that is, oral tablets, capsules, elixirs, syrups and the like, and consistent with conventional pharmaceutical practices.

The pharmaceutical compositions of the disclosure can be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, injections, emulsions, elixirs, suspensions or solutions. Formulations may optionally contain stabilizers, pH modifiers, surfactants, bioavailability modifiers and combinations of these.

Pharmaceutical formulations may be prepared as liquid suspensions or solutions using a sterile liquid, such as oil, water, alcohol, and combinations thereof. Pharmaceutically suitable surfactants, suspending agents or emulsifying agents, may be added for oral or parenteral administration. Suspensions may include oils, such as peanut oil, sesame oil, cottonseed oil, corn oil and olive oil. Suspension preparation may also contain esters of fatty acids, such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol. Ethers, such as poly(ethyleneglycol), petroleum hydrocarbons, such as mineral oil and petrolatum, and water may also be used in suspension formulations.

The compositions of this disclosure are formulated for pharmaceutical administration to a mammal, preferably a human being. Such pharmaceutical compositions of the disclosure may be administered in a variety of ways, preferably parenterally.

Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

In addition to dosage forms described above, pharmaceutically acceptable excipients and carriers and dosage forms are generally known to those skilled in the art and are included in the disclosure. It should be understood that a specific dosage and treatment regimen for any particular patient will depend upon a variety of factors, including the activity of the specific peptide employed, the age, body weight, general health, sex and diet, renal and hepatic function of the patient, and the time of administration, rate of excretion, drug combination, judgment of the treating physician or veterinarian and severity of the particular disease being treated.

In some embodiments, the composition can further include a secondary antimicrobial agent. Non-limiting examples of such agents include imipenem, ceftazidime, colistin, chloroquine, artemisinin, vancomycin and daptomycin.

5. Methods

Methods of using the peptides, compositions and formulations of the present disclosure are also described. In one embodiment, the methods are for preventing or treating an infection of a microorganism. The microorganism can be a bacterium, such as a Gram-negative bacterium, or a parasite (e.g., malaria-causing microorganisms). In some embodiments, the infection is multi-drug-resistant, such as one caused by multidrug-resistant *Pseudomonas aeruginosa* (MDRPA) or multidrug-resistant *Acinetobacter baumannii* (MDRAB).

The peptides, compositions and formulations are also useful for treating a disease or condition associated with an infection, such as wound abscess, catheter biofilm, pneumonia, and bacteremia.

In some embodiments, the treatment methods further include administration, concurrently or sequentially, of a second secondary antimicrobial agent. Non-limiting examples of such agents include imipenem, ceftazidime, colistin, chloroquine, artemisinin, vancomycin and daptomycin.

The peptides, compositions and formulations of the disclosure may be administered to the systemic circulation via parental administration. The term "parenteral" as used herein includes subcutaneous, intravenous, intramuscular, intra-articular, intra-synovial, intrasternal, intrathecal, intra-hepatic, intralesional and intracranial injection or infusion techniques. However, in cases where the infection is local (e.g., on the skin), the composition may be administered locally, such as topically.

EXAMPLES

Example 1. In Vitro Mechanistic Study

This example tested the antibacterial activity of two peptides, RP-1 and γ-RP-1, in vitro and assessed the multiparametric mechanisms of action (MOA) of these peptides. RP-1 has a nominal sequence of N-ALYKKFKKKLLK-SLKRLG-C(SEQ ID NO:3) and is a consensus sequence obtained from the α-helix motifs of multiple kinocidin proteins. γ-RP-1 (SEQ ID NO: 1) is a fusion that further includes, at the N-terminus of RP-1, a portion of the γ-core of the CXCL4 protein. The γ-core has not been shown to have anti-infective activities.

RP-1 and γ-RP-1 mechanisms were evaluated using a multi-parametric flow cytometry platform optimized to MDRPA and MDRAB. Included in these investigations were assessments of microbicidal vs. microbiostatic kinetics, membrane injury, energy decoupling, and mechanisms of ancient programmed cell death pathways (caspase/metacaspase induction and phosphatidylserine-like lipid accessibility). Mechanisms of action were determined alone and in combination with the conventional antibiotics (e.g., imipenem, ceftazidime, or colistin).

Figure 1B:
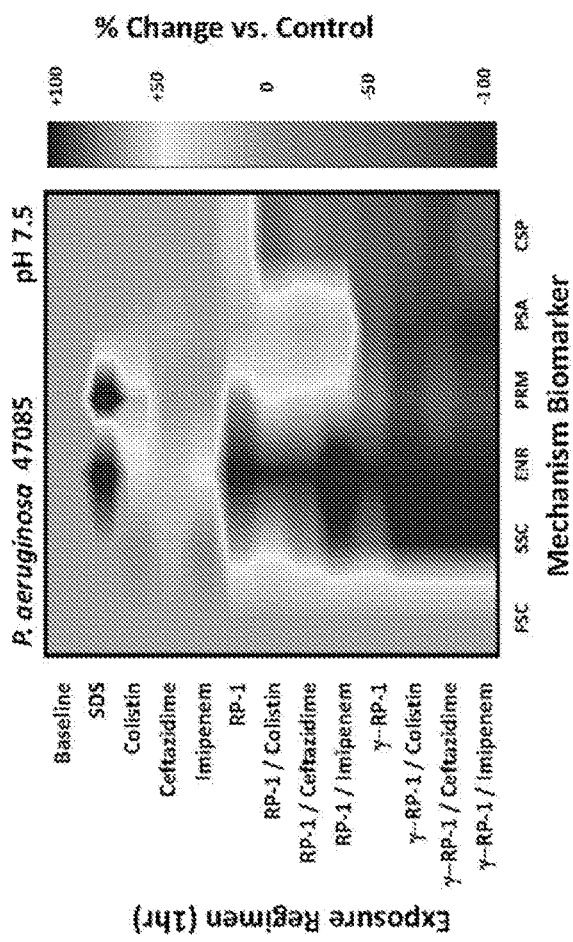
Figures 2, 3:
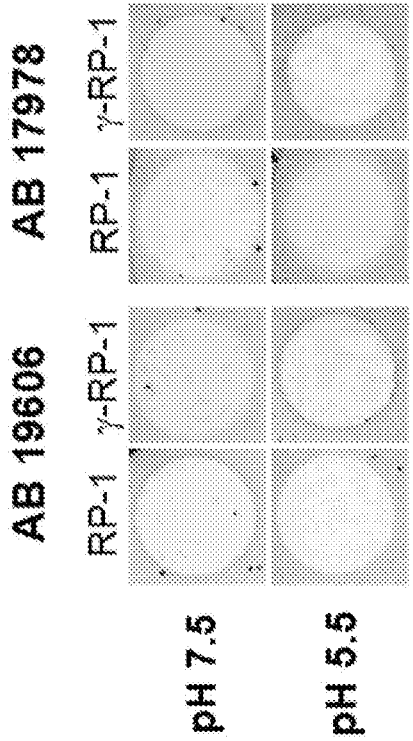
FIG. 2 shows the efficacy of RP-1 and γ-RP-1 against reference strains of MDRAB by radial diffusion in vitro.
FIG. 3 presents comparative MICs against reference strains of MDRAB using CLSI assay methods.
Figure 4:
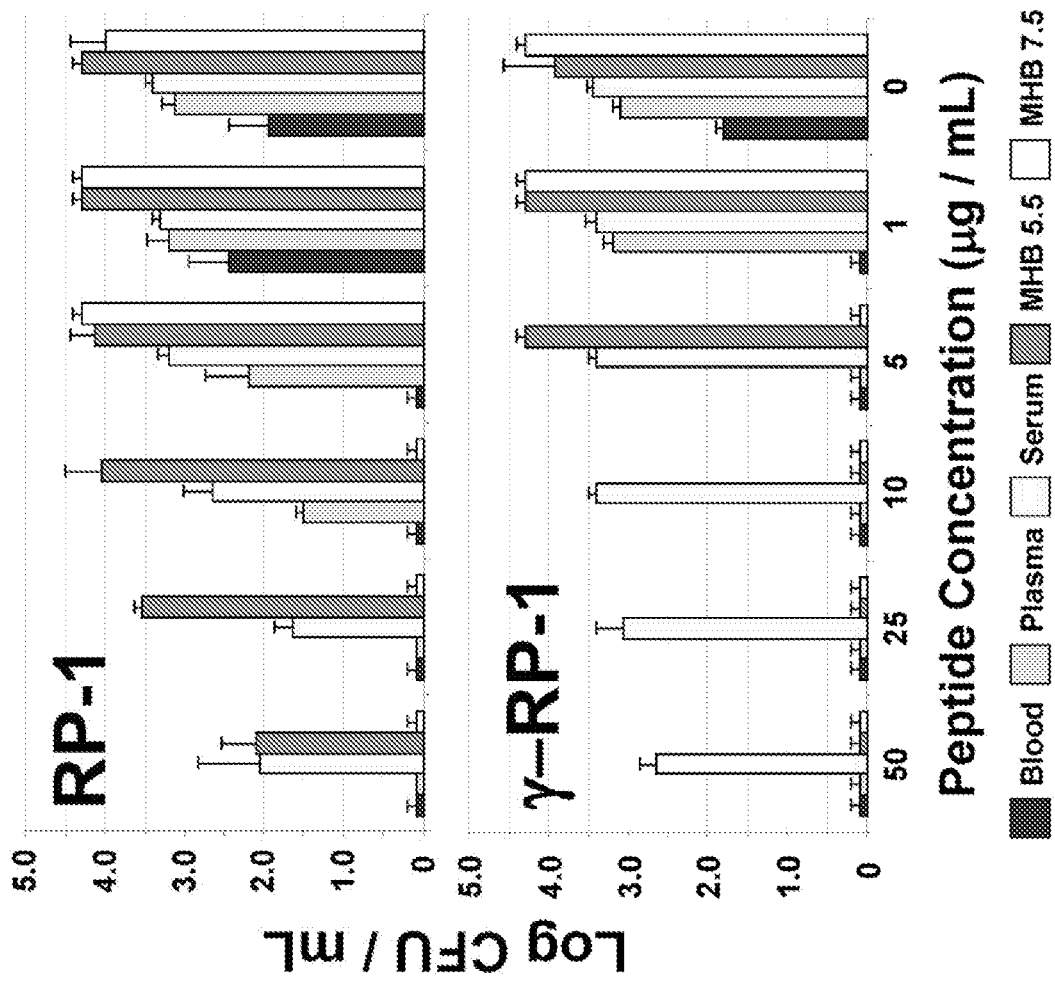
FIG. 4 shows peptide efficacies against a reference strain of MDRAB in human blood matrices.

FIGS. 1A and 1B illustrate the mechanisms of action (MOA) of RP-1 and γ-RP-1, assessed alone and combined with conventional antibiotics against prototypic strains of MDRPA (47085 or PA-01) and MDRAB (19606), in vitro by flow cytometry. Parameters evaluated: cell size (forward scatter [FSC]; osmostasis); cytoplasmic refractivity (side scatter [SSC]; DNA/RNA condensation); cellular/membrane energetics ($\Delta\psi$; [ENR]); cell membrane permeability (PRM); phosphatidylserine accessibility ([PSA]; programmed cell death pathway); caspase or metacaspase induction ([CSP]; programmed cell death pathway).

Increases in parameters measured are indicated by a red (gray in encircled areas) spectral shift, while decreases in parameters shift toward a violet spectrum (black in the top middle to left area); green (background gray) indicates no significant change from baseline. These data emphasize distinct, specific mechanistic signatures of metapeptides. Each graph integrates more than 1.2 million data points, generated using a multi-color flow cytometry and analytical methodologies.

This example compares the metapeptides (RP-1 and γ-RP-1) alone, relevant standard antibiotics alone (imipenem, ceftazidime, colistin), versus combinations of metapeptides plus antibiotics. The study assessed metapeptide impact on multiple aspects of target cell function: osmostasis, cytoplasmic/nucleic acid condensation, energetics, membrane permeabilization, phosphatidyl serine-like lipid turnover and metacaspase or caspase-like activation (surrogate biomarkers of programmed cell death). The results show that 1) RP-1 and γ-RP-1 have specific mechanisms and are not indiscriminant membrane detergents; 2) mechanisms of action differ considerably from those of conventional antibiotics; and 3) γ-RP-1 and RP-1 mechanisms differ against MDRPA vs. MDRAB.

Example 2. Efficacy of Intravenous Kinocidinsin a Neutropenic Murine Model of Multi-Drug-Resistant *Acinetobacter baumannii* Pneumonia This example tested the efficacy of RP-1 and γ-RP-1 in a neutropenic murine model of multi-drug-resistant *Acinetobacter baumannii* pneumonia.

Methods and Materials

Bacterial strains and sources used in this example are listed below:

| Study Strains | Human Source |
|---|---|
| AB19606 | Blood/Urine |
| AB17978 | Meningitis |
| AB-HUMC-1 | Bacteremia |

Log-phase cells (BHI; 37° C.) were cultured from master cell banks, sonicated and quantified by spectrophotometry to a desired CFU.

Antimicrobial agents: RP-1 (pI/Mw: 10.82/2162.78 Da) is an 18-amino synthetic peptide derived from PF-4 family kinocidins. γ-RP-1 (pI/Mw: 10.64/4444.5 Da) is a 39-amino synthetic peptide comprising a CXCL4 kinocidin γ-core motif-RP-1 construct. Stock peptides dissolved in sterile ddH$_2$O were diluted in suitable buffers. Antibiotics were purchased as purified powder and re-suspended in PBS per the manufacturer guidelines.

Radial Assay:

RP-1 and γ-RP-1 efficacy was evaluated by radial diffusion at pH 5.5 or 7.5. Log-phased organisms were inoculated in buffered agarose and plated. Study peptides (10 μg/well) were introduced into wells in seeded matrix and incubated (3 hr, 37° C.). After overlay of nutrient medium (TSA), the assays were incubated (24 hr) and zones of inhibition defined as radius (mm) of complete clearance minus the well radius. Independent minimum, n=2.

CLSI Assay:

RP-1 and γ-RP-1 were evaluated for their minimum inhibitory concentrations (MIC) per CLSI standards in MHB across a 100-0.19 m/ml range. Independent minimum, n=2.

Biomatrix Assay:

Efficacies of RP-1 and γ-RP-1 in human blood, plasma, or serum were assessed. Peptide was added to biomatrix simultaneously with MDRAB (final inoculum $10^5$ CFU/ml; peptide range 1-50 m/ml; volume 100 μl). Controls were performed using Mueller Hinton broth (MHB; CLSI). Following incubation (constant agitation; 2 h, 37° C.), survival was quantified by culture (n=3) upon blood agar and defined as CFU/ml. Independent minimum, n=2.

Mechanisms of Action.

Peptide or antibiotic mechanisms versus MDRAB were studied by flow cytometry: 1) forward scatter (FSC; osmostasis); 2) side scatter (SSC; cytoplasmic condensation); 3) energetics (ENR; cytoplasmic membrane [CM] potential); 4) CM permeabilization (PRM); 5) phosphatidylserine accessibility (PSA; lipid turn over associated with autolysis); and 6) caspase-and/or metacaspase-like activation (CSP; programmed cell death).

Neutropenic Pneumonia.

Neutropenic mice (cortisone acetate [250 mg/kg; subQ]+ cyclophosphamide [200 mg/kg; IP] on study days-2, +3, and +8) were infected on day 0 (aerosolized; MDRAB clinical isolate HUMC-1; $5 \times 10^8$ CFU; lung Cx-positive). Treatment initiated 4 hr or 24 hr post-infection and continued for 3d. Groups:control (PBS); imipenem (15 mg/kg; IP; bid); γ-RP-1 (12.5 mg/kg; IV; qd); γ-RP-1 (12.5 mg/kg; IV; qd). Survival was then monitored to day 21. At end point or 21d, lungs and spleens were cultured. Outcomes were compared by non-parametric analysis. All studies adhered to institutional and AAALAC animal care policies.

Results

Figure 6:
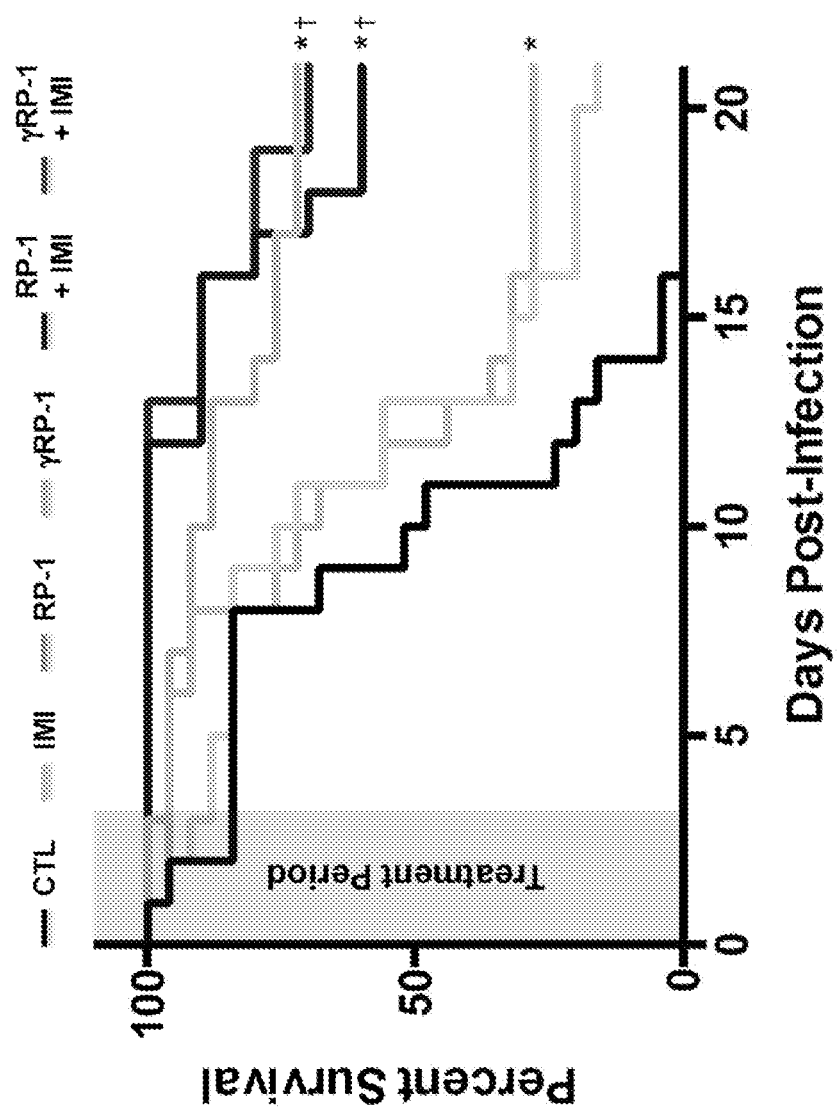
FIG. 6 compares peptide or imipenem efficacy against a reference strain of MDRAB in neutropenic pneumonia in vivo.
Figure 7:
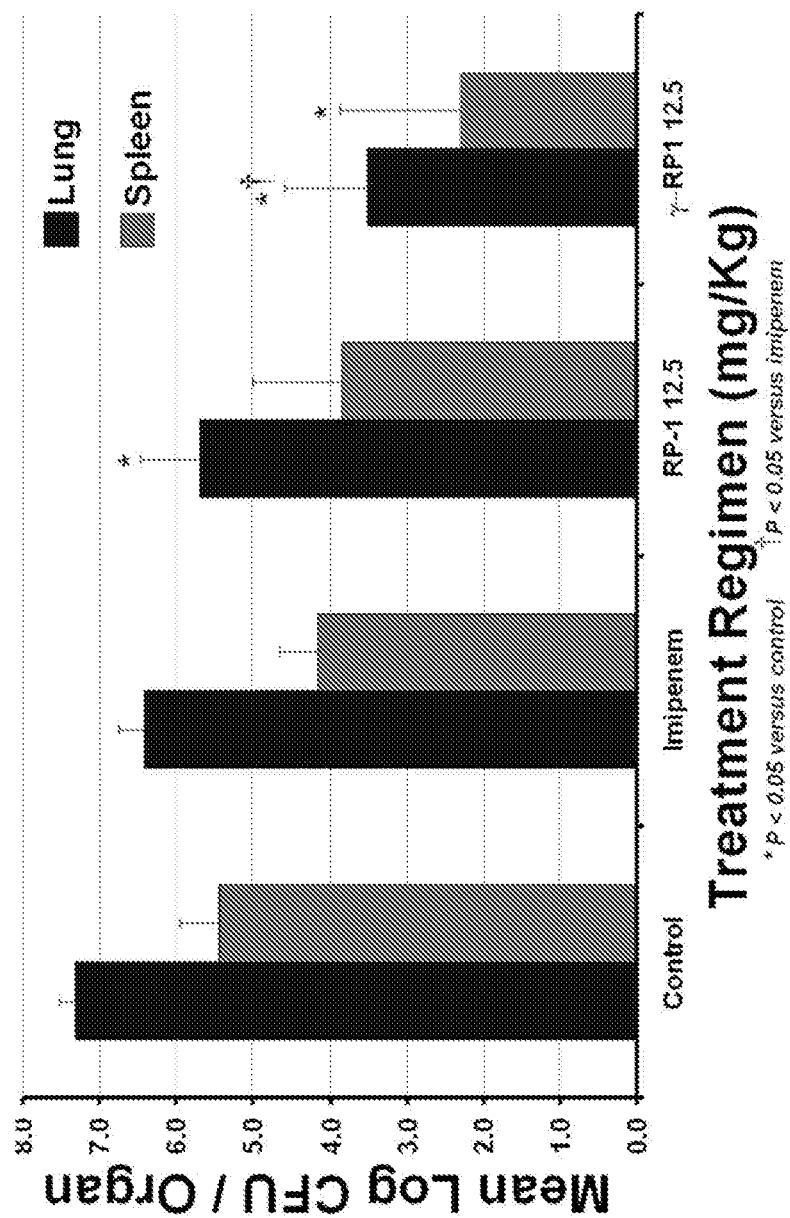
FIG. 7 compares the efficacy of peptide or imipenem against a reference strain of MDRAB in representative tissues (lung, spleen) in vivo.
Figure 8:
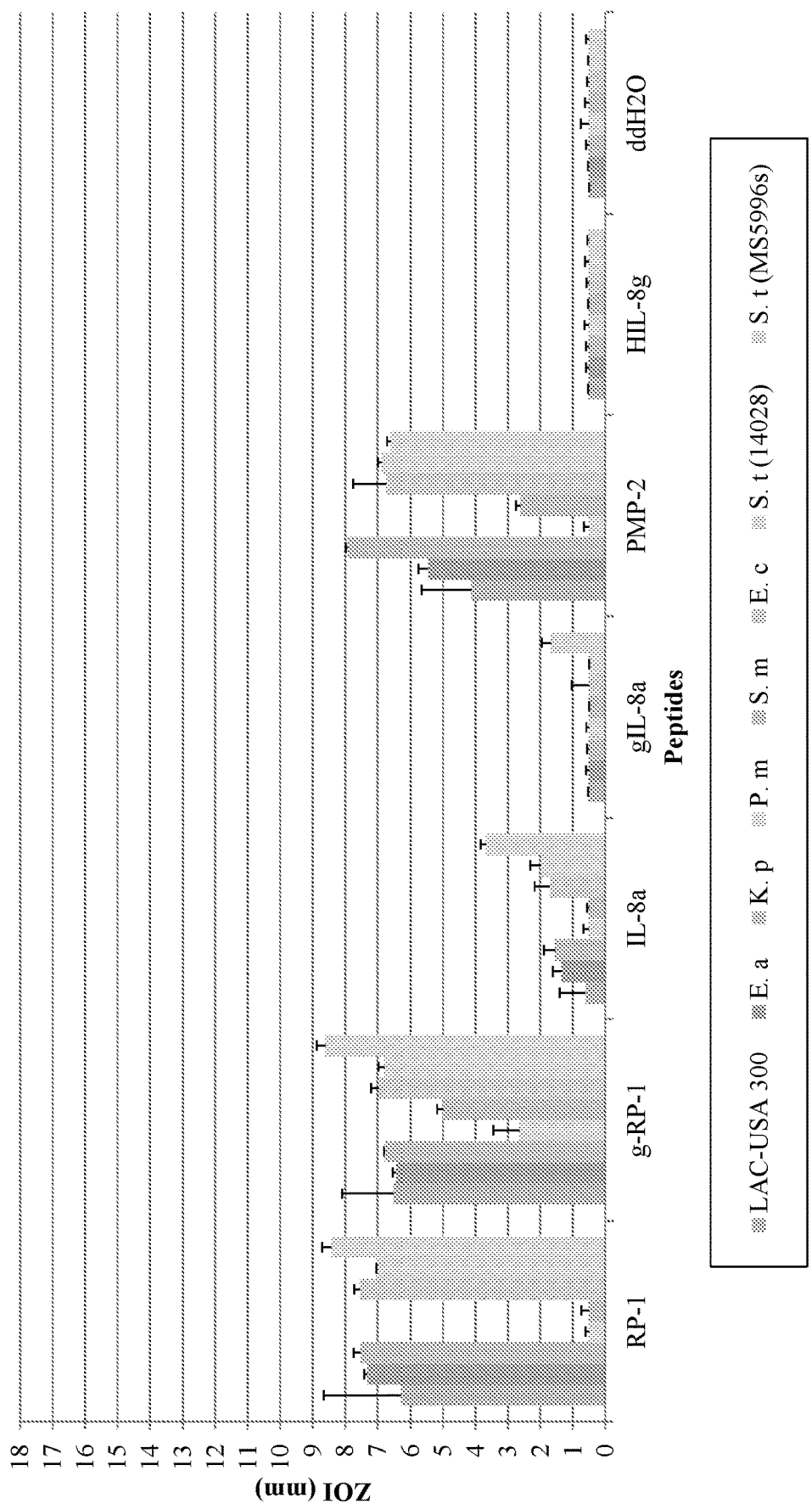
FIG. 8-11 present charts showing the efficacy of different peptides against a panel of Gram-negative human pathogens under differing conditions of pH (5.5 or 7.5) in vitro.
Figure 9:
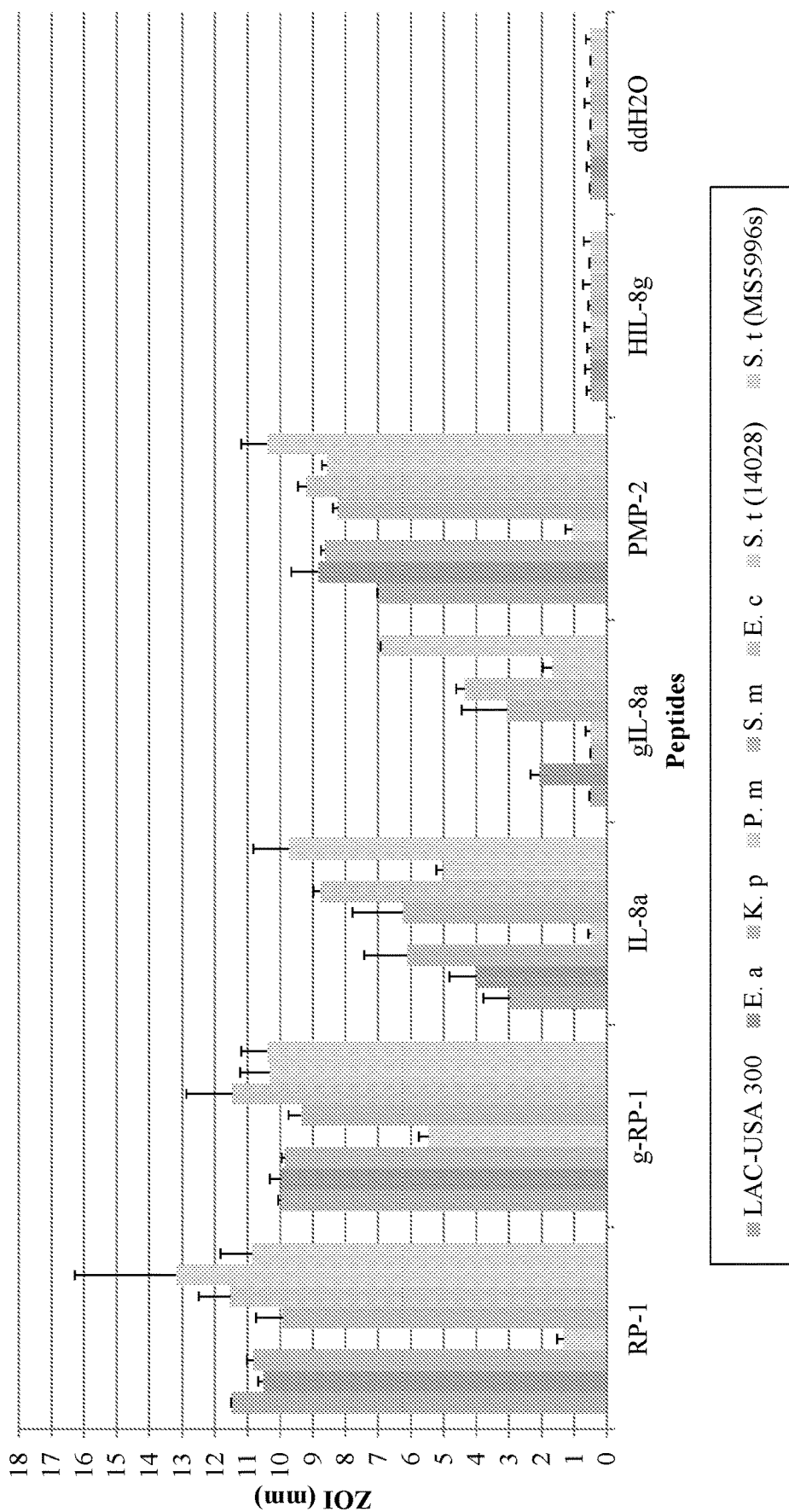
Figure 10:
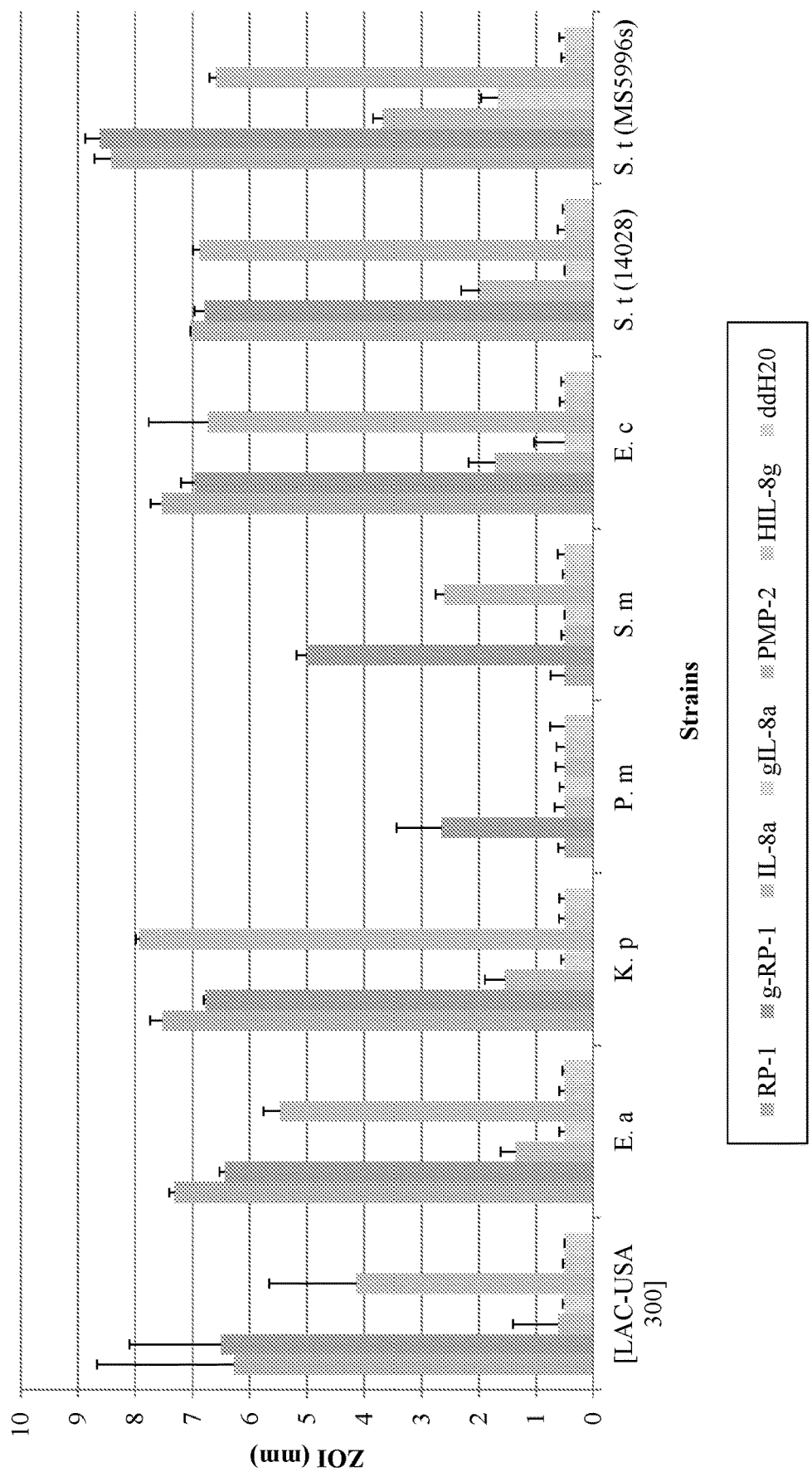
Figure 11:
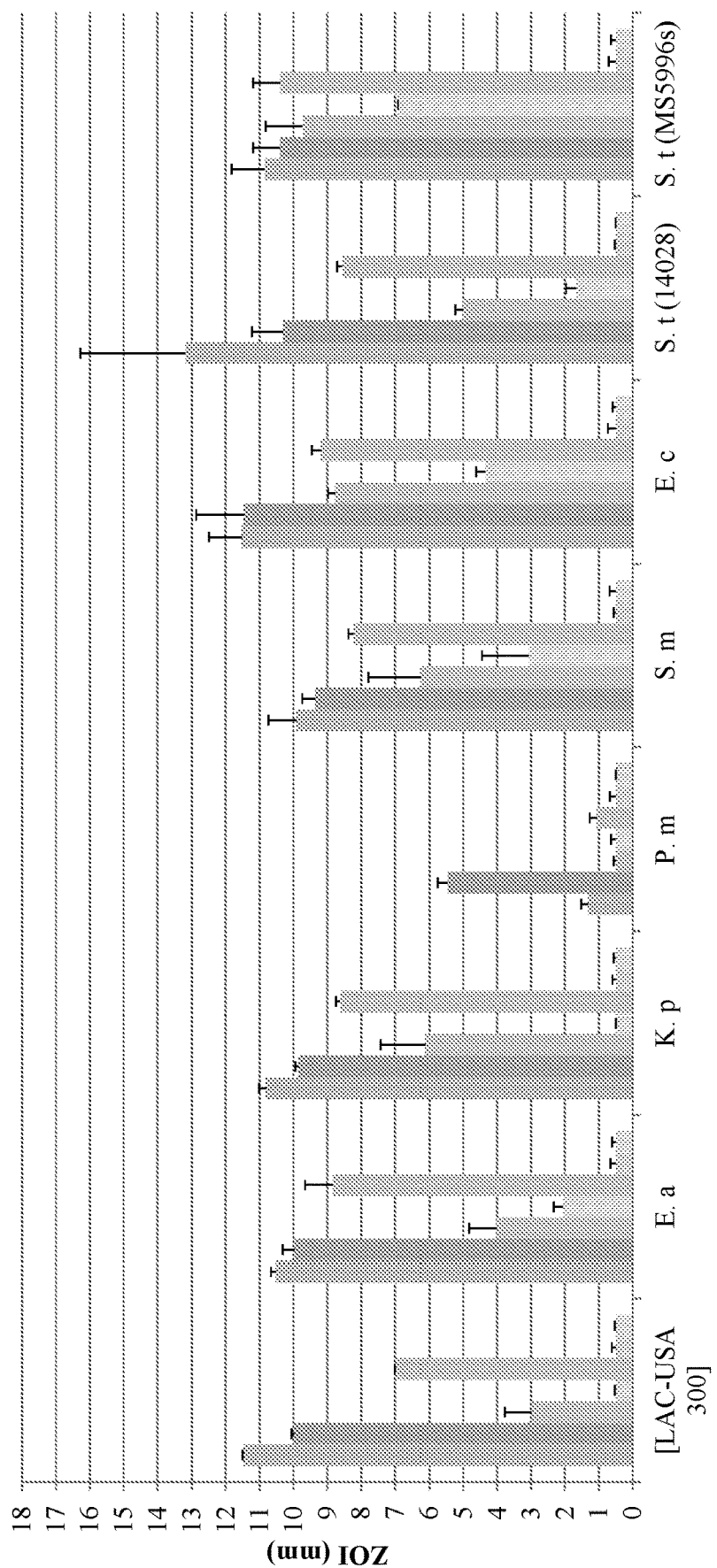

Control or imipenem-treated mice had 0% or 16% survival, respectively (FIG. 6). RP-1 or γ-RP-1 treatment alone had 28% (p<0.01 vs. control) or 72% (p<0.01 vs. control or imipenem) survival, respectively (FIG. 6). The combinations of RP-1 or γ-RP-1 with imipenem treatment achieved respective 60% or 75% survival rates (p<0.01 vs. control or imipenem, FIG. 6). Total MDRAB burden (CFU) in lungs and spleens were significantly reduced (>2 log CFU) in γ-RP-1 and combination treatment groups as compared to control or imipenem treatments alone.

Figure 5:
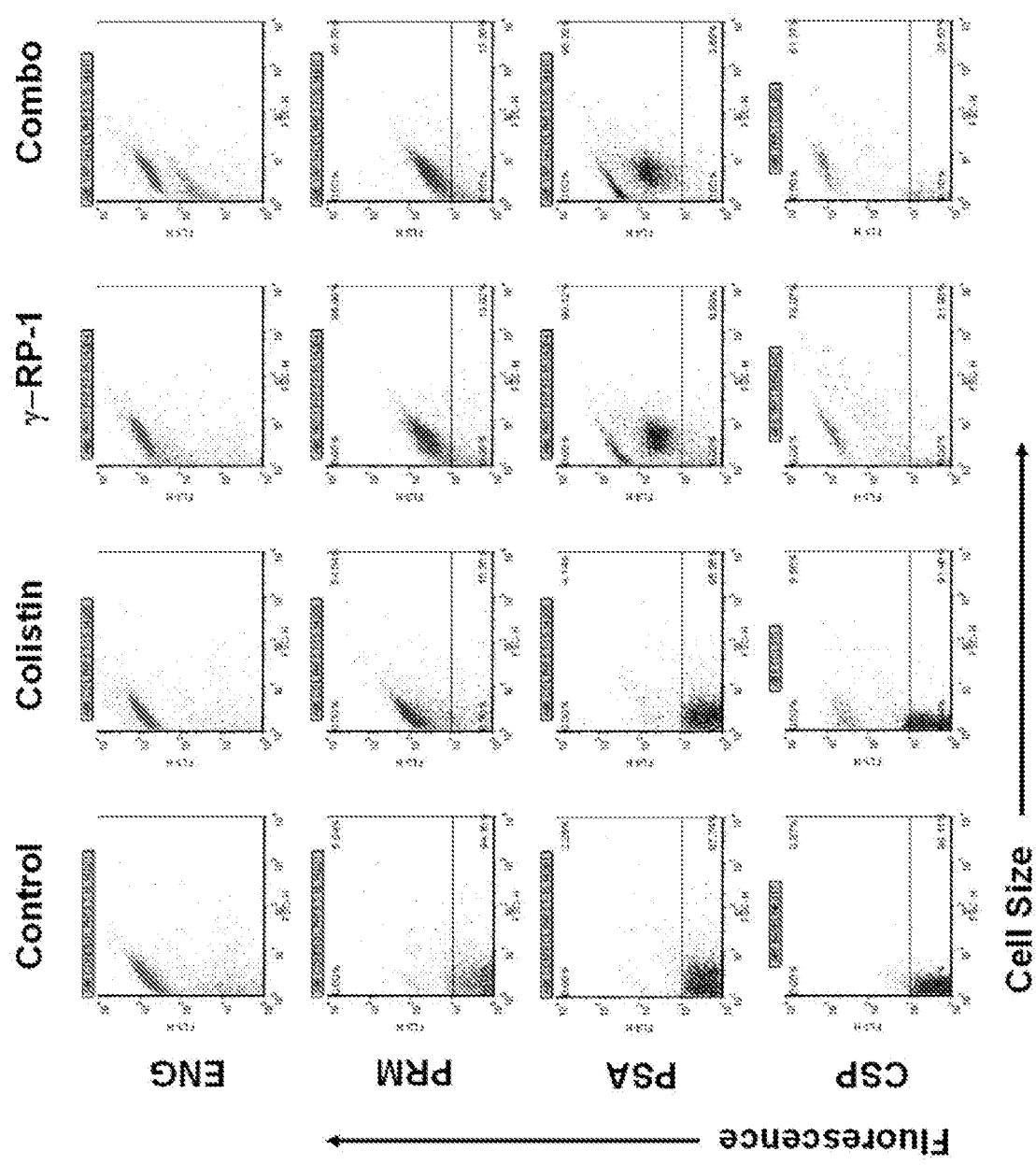
FIG. 5 presents charts showing mechanisms of peptide or antibiotic action (MOA) against a reference strain of MDRAB in vitro.

FIGS. 2-4 and 6-7 show that RP-1 and γ-RP-1 have significant efficacy vs. MDRAB in human blood ex vivo and in a murine model of neutropenic pneumonia. RP-1 and γ-RP-1 mechanisms of action versus MDRAB involve multiple targets, including cell membrane perturbation, energy dysfunction and programmed cell death (FIG. 5).

The systemic (IV) administration of γ-RP-1 alone or either kinocidin in combination with imipenem achieved robust efficacy vs. MDRAB pneumonia in an otherwise lethal neutropenic murine model. These outcomes affirm RP-1 and γ-RP-1 as innovative and efficacious biologic candidates for further evaluation to address the looming threat of MDRAB infections.

The present data further substantiate the γ-RP-1 peptide as overcoming many historic barriers to anti-infective peptide development, including systemic (IV) durability, safety and efficacy in a highly rigorous model of established infection in a significantly immunocompromised host.

Example 3. RP-1 and γ-RP-1 Efficacy in Mouse Model of MDRPA Skin Infection

In addition to the studies in Example 2 examining systemic efficacy, this example advanced investigations in which RP-1 and γ-RP-1 were evaluated for topical efficacy in MDRPA skin/skin structure infection (SSSI).

This example first assessed several topical vehicles, and identified 20% P188 poloxamer as appropriate for pre-clinical research, having been tested in humans, low cost, excellent solubility of peptides, rapid absorption, and no inhibition of peptide antimicrobial activity. In this murine SSSI model, flanks were shaved and MDRPA ($6 \times 10^5$ CFU; log phase) introduced subcutaneously 4 or 24 hr prior to initiation of peptide treatment. To address any potential immunostimulation effects that may be caused by the peptides, a strength of the model treats one flank with vehicle alone, and the contralateral flank of the same animal with vehicle+peptide (100 μg). Preliminary data demonstrated strong efficacy in reduction of lesion severity and CFU/abscess, with no apparent skin toxicity due to either peptide.

Pilot studies were also conducted to assess peptide efficacy in SSSI due to methicillin-resistant *S. aureus* (MRSA). First, the vehicle (20% P188 poloxamer) did not inhibit metapeptide activity vs. a prototype MRSA strain that caused significant human SSSI, namely LAC-USA300. Compared to PBS, the vehicle allowed excellent solubility and did not inhibit anti-MRSA activity of either RP-1 or g-RP-1. Next, this example tested efficacy of topical formulations of the peptides in pilot studies using the same model system as above (MRSA inoculum, $3 \times 10^7$ CFU). Results demonstrated that the peptides exerted significant efficacy in suppressing MRSA lesion severity over 7 days.

Example 4. Efficacy of RP-1 and γ-RP-1 in a Wide Panel of Gram-Negative Pathogens The efficacy of RP-1 and γ-RP-1, along with a number of peptide variants and suitable control, was tested against a wide panel of Gram-negative human pathogens. The peptides are listed in the table below.

| Peptide | Remark |
|---|---|
| RP-1 | RP-1 (SEQ ID NO: 3) |
| γ-RP-1 | γ-RP-1 (SEQ ID NO: 1) |
| IL-8-α | α-helix of human IL-8 (KENWVQRVVEKFLKRAENS, SEQ ID NO: 9) |
| γ-IL-8α | γ IL-8α (ANTEIIVKLSDGRELCLDPKENWVQRVVEKFLKRAENS, SEQ ID NO: 10) |
| PMP-2 | Comparative rabbit CXCL4 template domain (NLIATKKNGRKLCLDLQAALYKKKIIKKLLES, SEQ ID NO: 11) |
| hIL-8-γ | γ core of human IL-8 (ANTEIIVKLSDGRELCLDP, SEQ ID NO: 12) |
| ddH₂O | control |

The following table lists the organisms tested:

| Peptide | Remark |
|---|---|
| USA300 | LAC-USA300 MRSA control |
| E.a. | *Enterobacter aerogenes* |
| K.p. | *Klebsiella pneumoniae* |
| P.m. | *Proteus mirabilis* |
| S.m. | *Serratia marcenscens* |
| E.c. | *Escherichia coli* |
| S.t.R | *Sal. typhimurium* 14028-R |
| St.S | *Sal. typhimurium* MS5996-S |

The testing results (at pH 5.5 and 7.5) are shown in FIG. 8-11. The results demonstrate that γ-RP-1 has the overall best efficacy against individual organisms, and across the broader panel, as compared to any other peptide tested in this study series.

Example 5. In Vitro and In Vivo Anti-Malaria Activity of γ-RP-1

Figure 12:
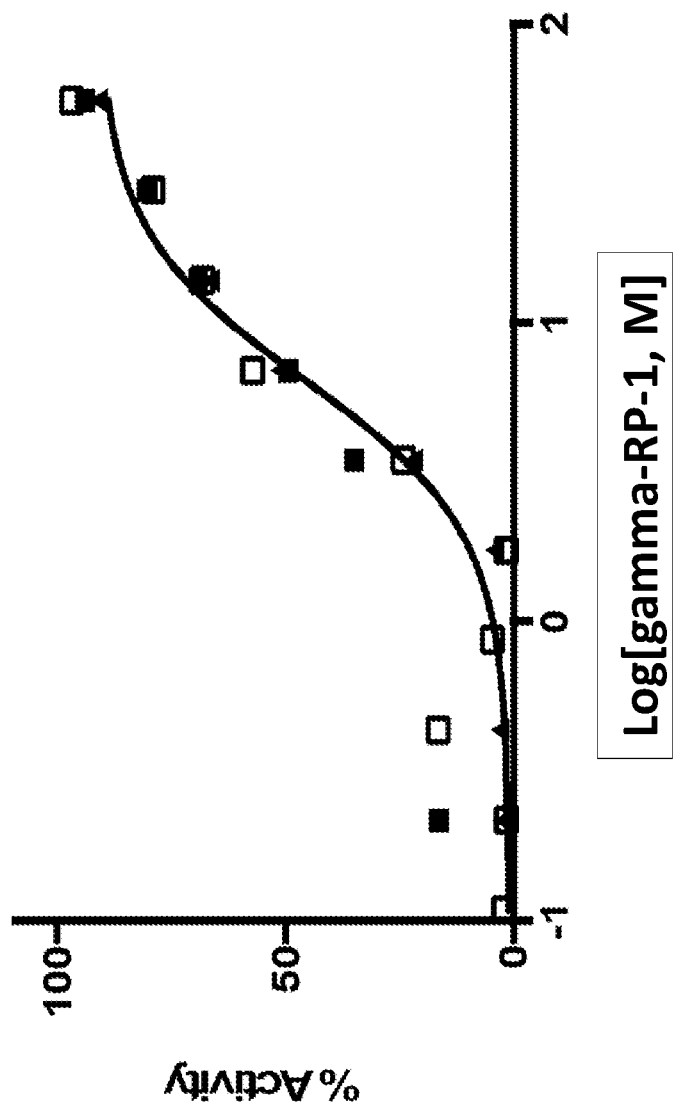
FIG. 12 shows a curve demonstrating the quantitative in vitro antimalarial activity of γ-RP-1 on 3D7 *P. falciparum.*
Figure 13:
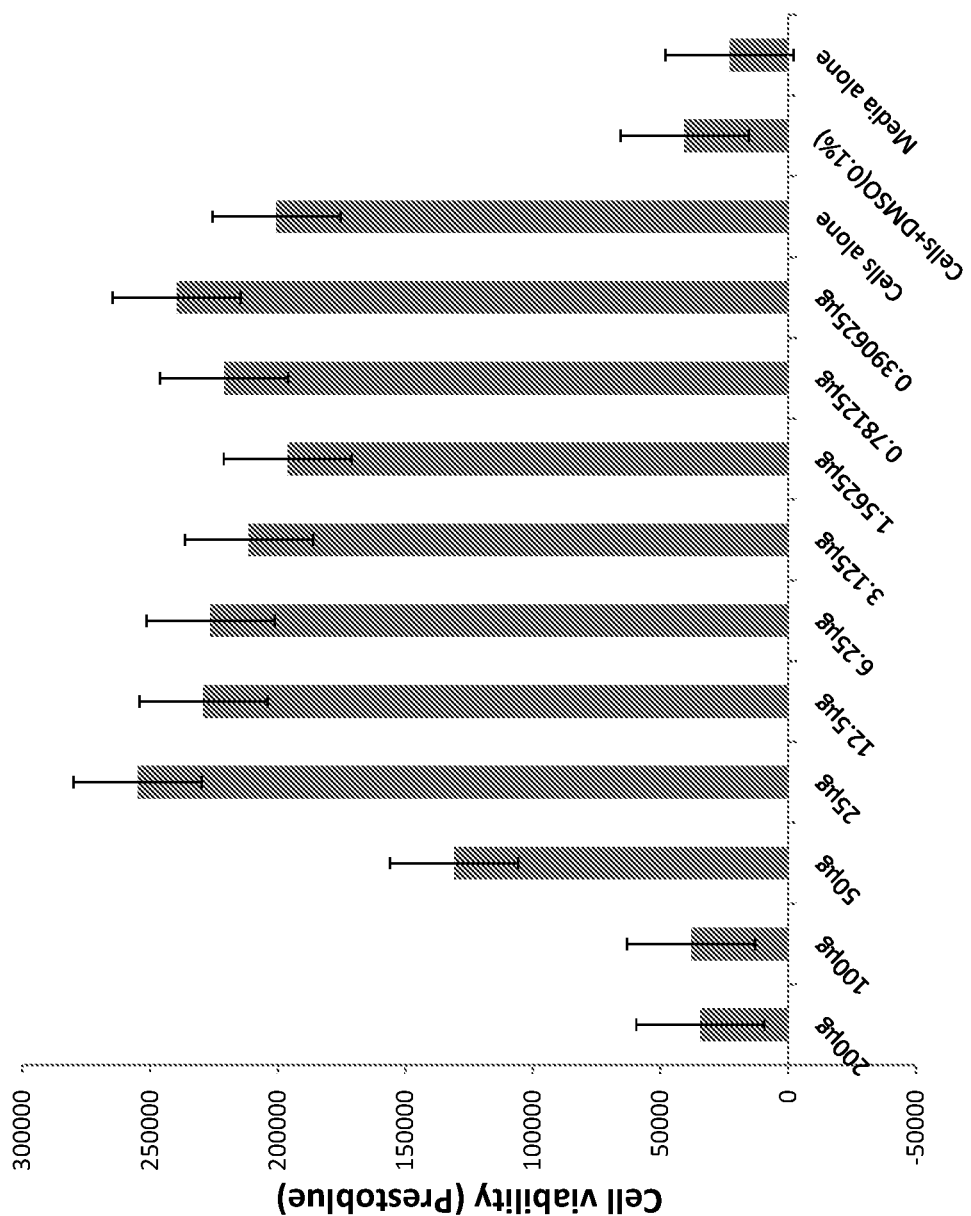
FIG. 13 shows in vitro tolerability data of γ-RP-1 on Human Brain Endothelial Cells (HBECs).

This example tested the anti-malaria activity of γ-RP-1. FIG. 12 shows the in vitro antimalarial effects of γ-RP-1 on 3D7 *P. falciparum*. The dose-response curve indicates excellent IC$_{50}$ curve in vitro at 12.5 mg/ml after incubation for 96 hour (two experiments in triplicate). FIG. 13 shows the results of an in vitro toxicity assay of γ-RP-1 on Human Brain Endothelial Cells (HBECs). This chart shows low toxicity for HBECs in vitro at 12.5 mg/ml after incubation for 96 hours (two experiments in triplicate).

Figure 14:
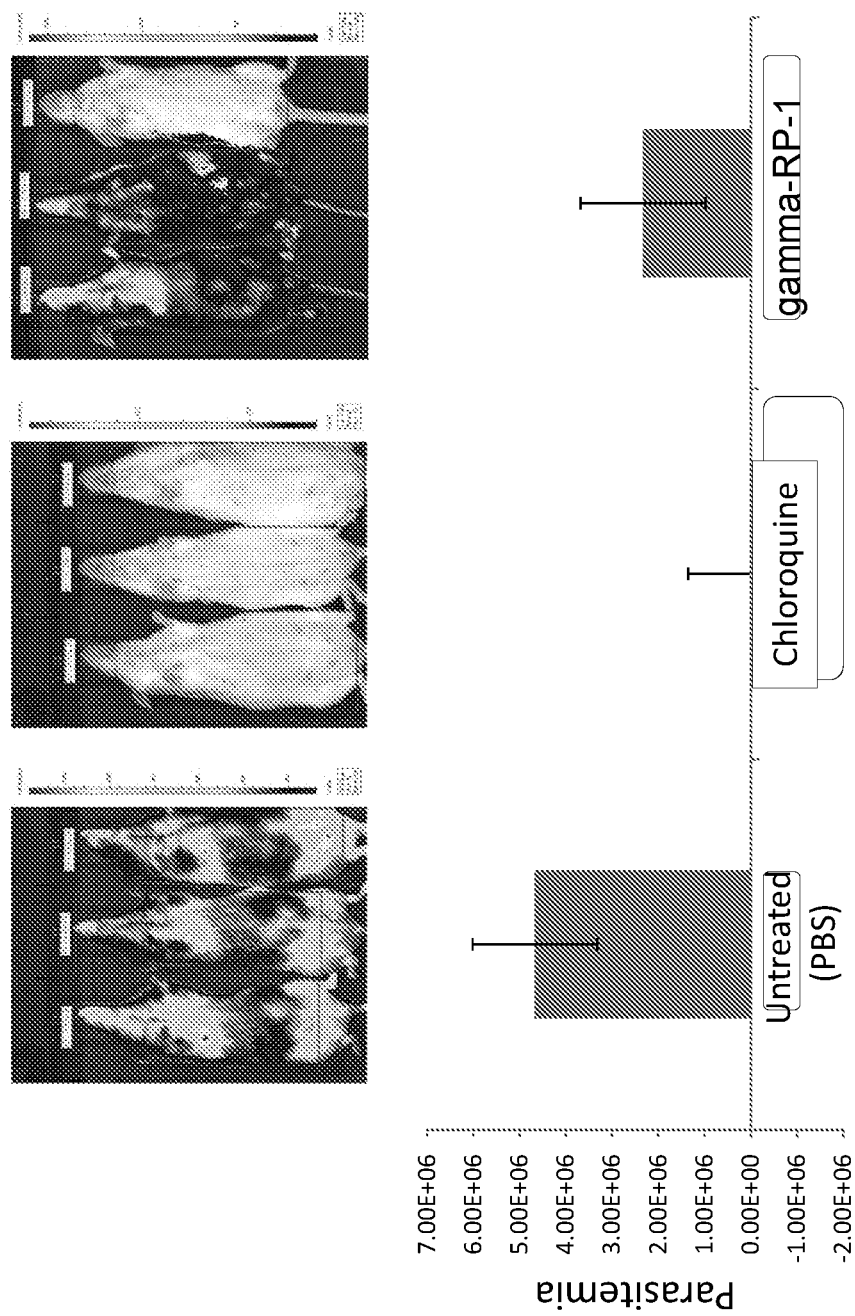
FIG. 14 shows the in vivo antimalarial efficacy of γ-RP-1 versus chloroquine on *P. berghei* ANKA luciferase infected Swiss Webster mice.
Figure 15:
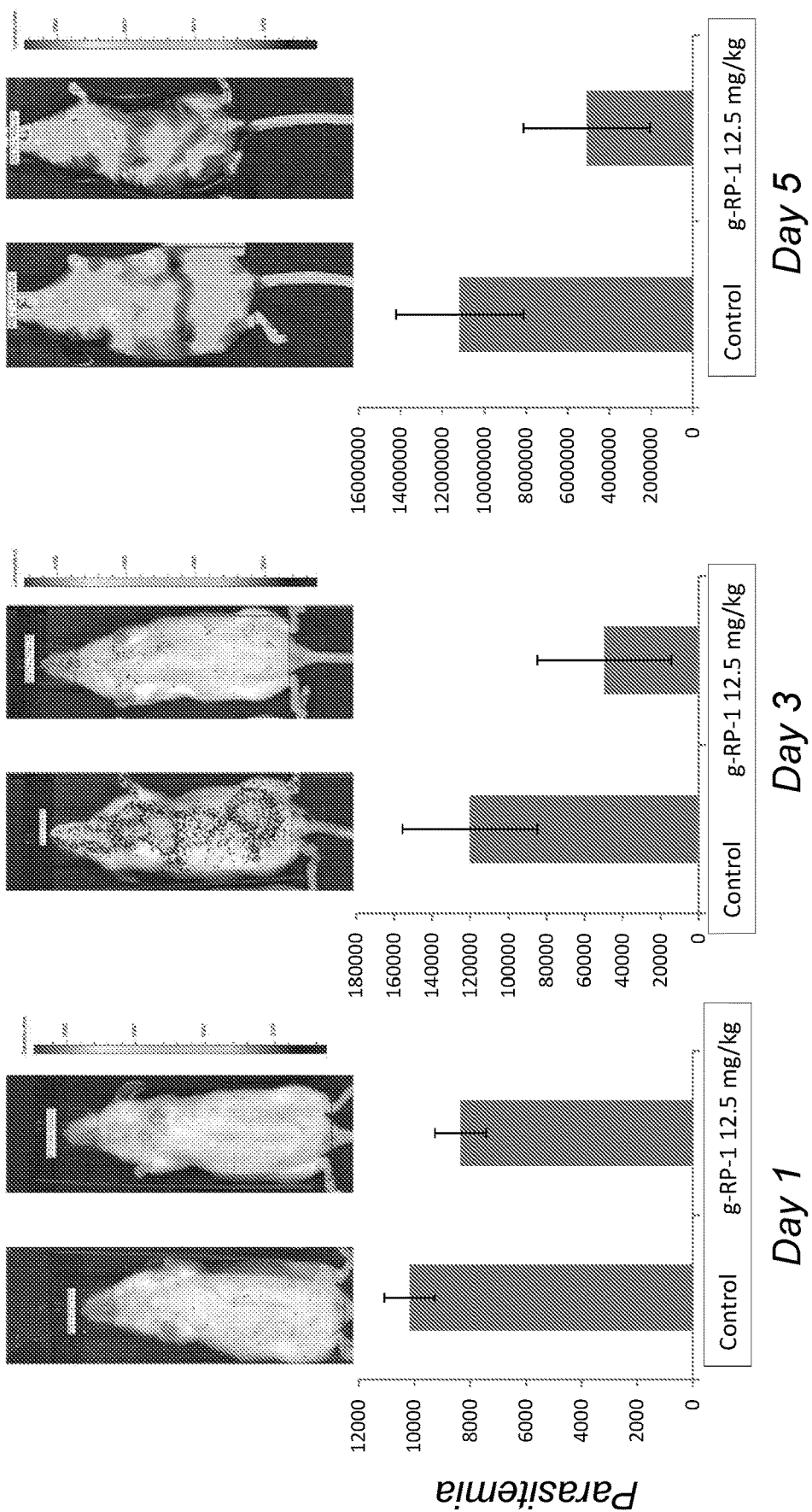
FIG. 15 shows the in vivo antimalarial activity of γ-RP-1 on Luciferase-expressing *P. berghei* ANKA (single dose).

In in vivo experiments, FIG. 14 presents images and bar graphs to show the moderate antimalarial activity in vivo at 12.5 mg/kg for γ-RP-1 compared to chloroquine at the same concentration (five mice in each group, IV treatment daily for 5 days). FIGS. 15 and 16 show the in vivo antimalarial activity of γ-RP-1 on Luciferase-expressing *P. berghei* ANKA (FIG. 15: single dose; FIG. 16: double dose). CQ: chloroquine.

These data demonstrate γ-RP-1's efficacy in treating chloroquine- or artemisinin-resistant malaria.

Example 6. Efficacy of γ-RP-1 and its Variants in a Wide Panel of Gram-Negative Pathogens The efficacy of RP-1 and γ-RP-1, along with a number of peptide variants and suitable control, was tested against a wide panel of human pathogens. The peptides are listed in the table below.

| Peptide | Remark |
|---|---|
| RP-1 | RP-1 (SEQ ID NO: 3) |
| g-RP-1 | γ-RP-1 (SEQ ID NO: 1) |
| g-A-RP-1 | CPTAQLIATLKNGRKICLDLQAALYKKFKKKLLKSLKRLG (SEQ ID NO: 13) |
| g-P-RP-1 | CPTAQLIATLKNGRKICLDLQPALYKKFKKKLLKSLKRLG (SEQ ID NO: 14) |
| 17P-g-RP-1 | CPTAQLIATLKNGRKIPLDLQALYKKFKKKLLKSLKRLG (SEQ ID NO: 15) |
| ddH₂O | control |

As compared to γ-RP-1 (g-RP-1), g-A-RP-1 includes an additional alanine at the C-terminus of the γ-core, g-P-RP-1 includes an additional proline at the C-terminus of the γ-core, and 17P-g-RP-1 replaces Cys17 of the γ-core with a proline.

Figure 16A:
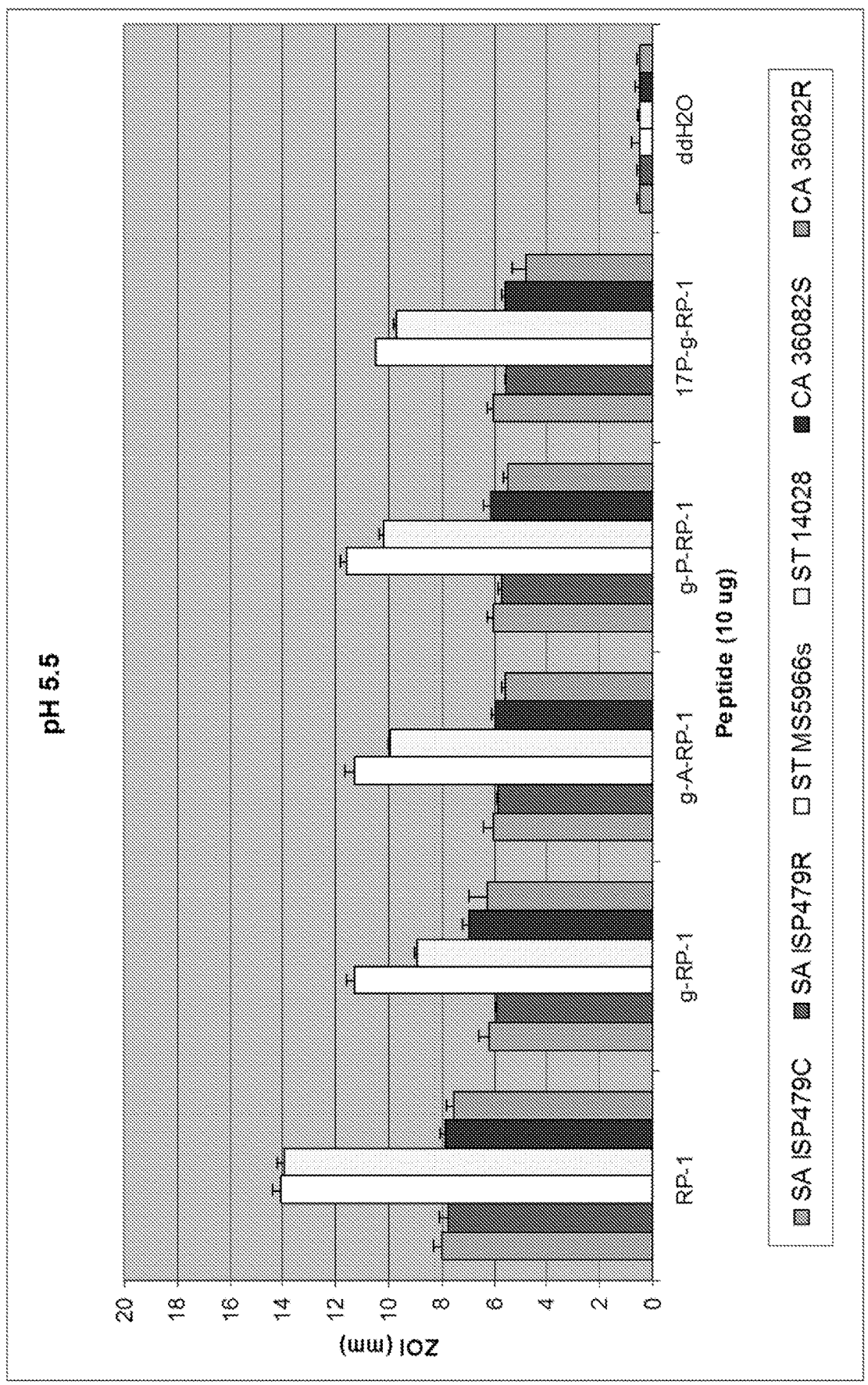
FIG. 16A-B present charts showing the efficacy of different peptides against a panel of Gram-negative human pathogens under differing conditions of pH (5.5 or 7.5) in vitro.
Figure 16B:
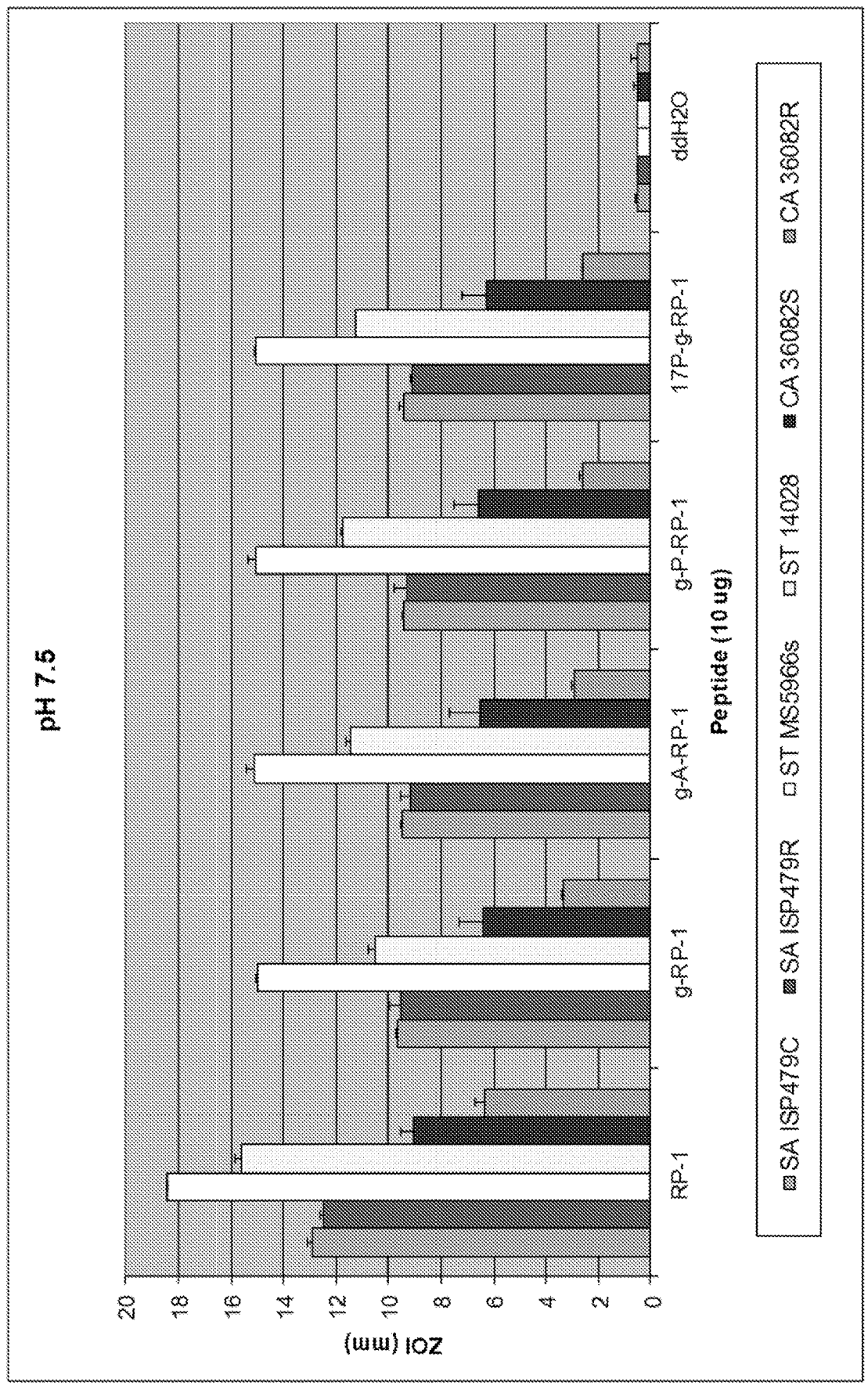

The testing results (at pH 5.5 and 7.5) are shown in FIG. 16A-B. The results demonstrate that γ-RP-1, as long as its variants g-A-RP-1, g-P-RP-1, and 17P-g-RP-1, all exhibited higher efficacy than RP-1, across bacterial species.

In another experiments, the following peptides were tested.

| Peptide | Remark |
|---|---|
| g-RP-1 | γ-RP-1 (SEQ ID NO: 1) |
| g-RP-1 (genscript) | γ-RP-1 (SEQ ID NO: 1) |
| g-AP-RP-1 | CPTAQLIATLKNGRKICLDLQAPALYKKFKKKLLKSLKRLG (SEQ ID NO: 16) |
| 14P-g-RP-1 | CPTAQLIATLKNGPKICLDLQALYKKFKKKLLKSLKRLG (SEQ ID NO: 17) |
| ddH₂O | control |

Figure 17A:
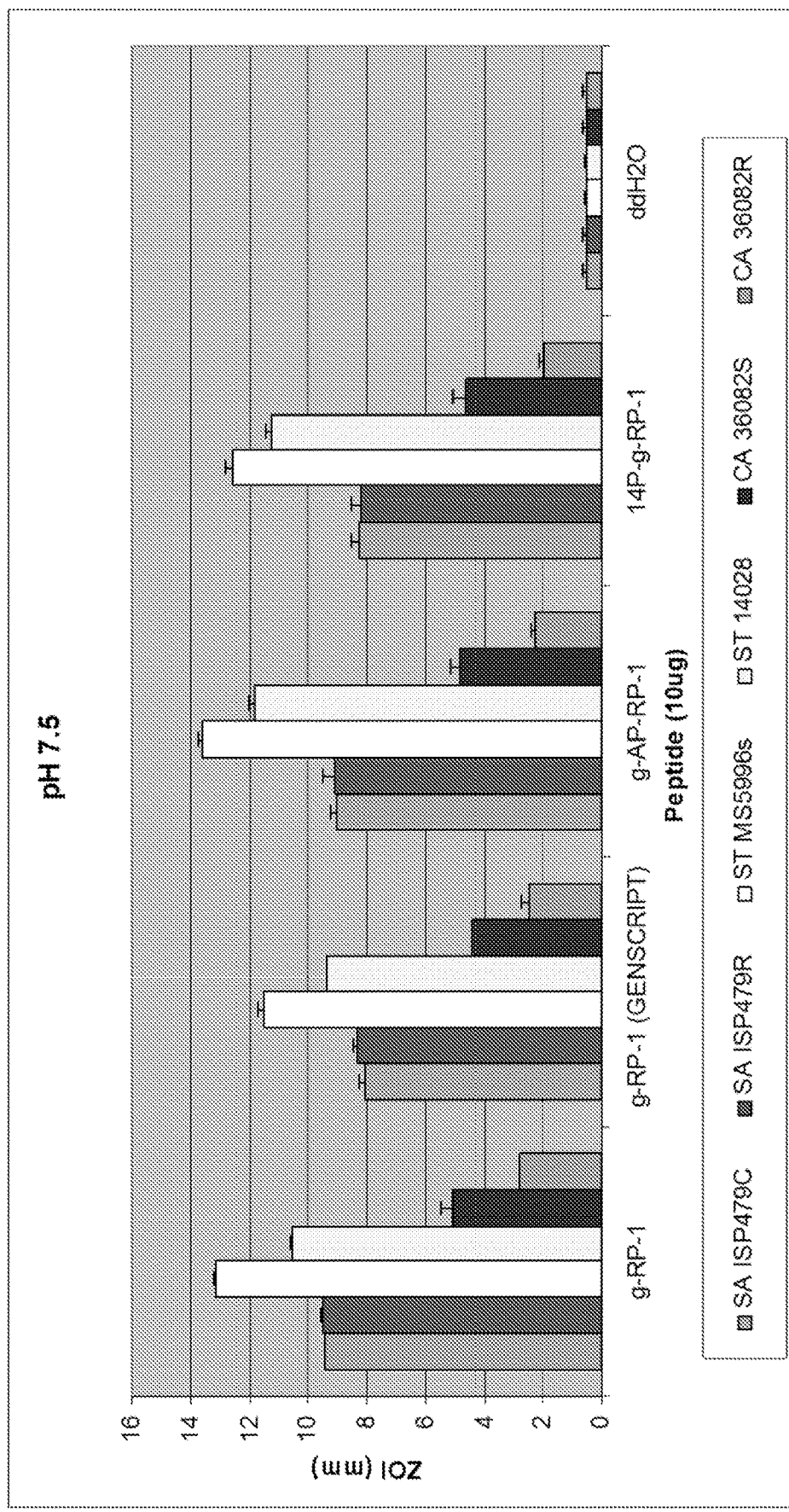
FIG. 17A-C present charts showing the efficacy of different peptides against a panel of Gram-negative human pathogens under differing conditions of pH (5.5 or 7.5) in vitro.
Figure 17B:
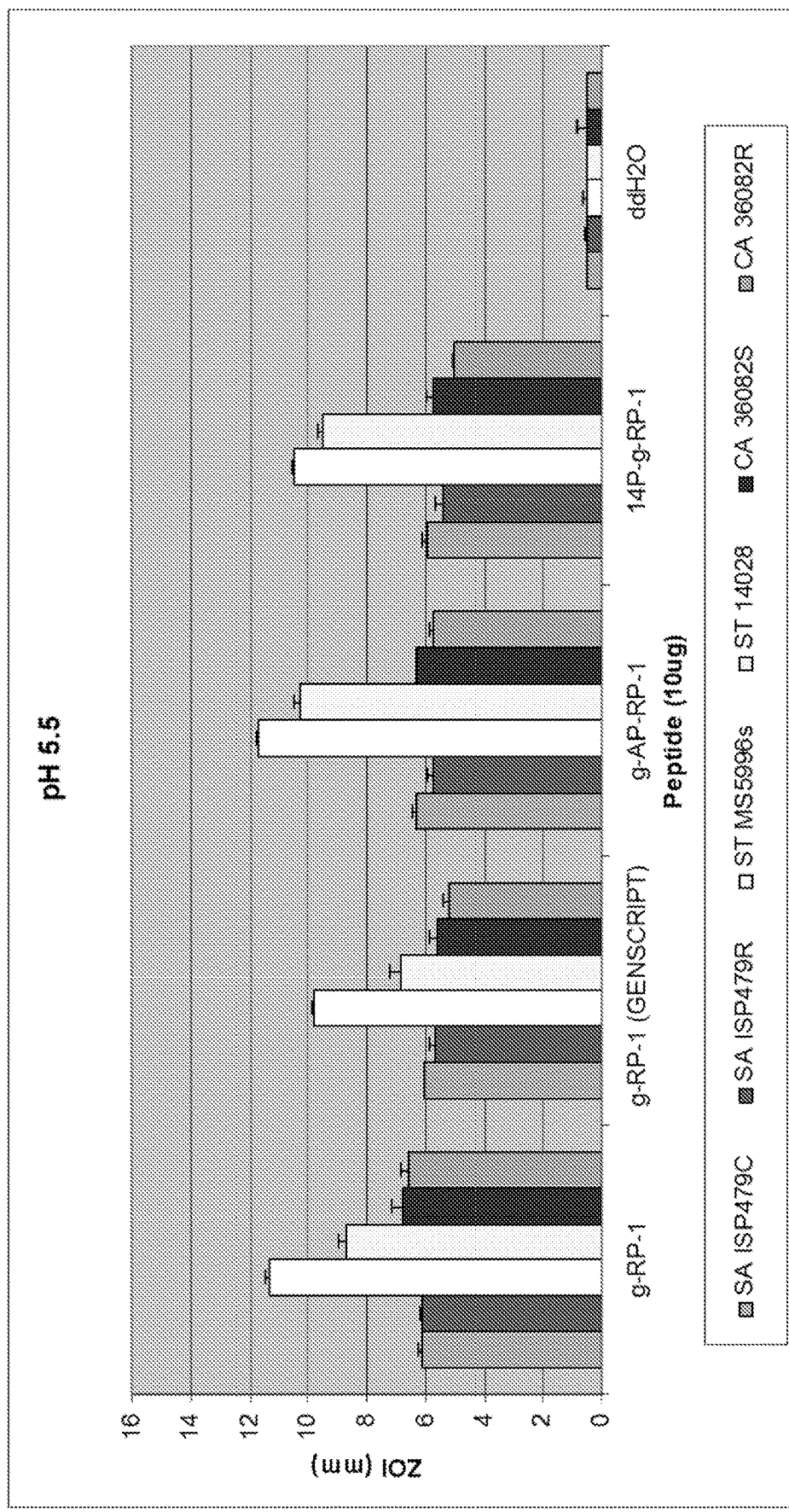
Figure 17C:
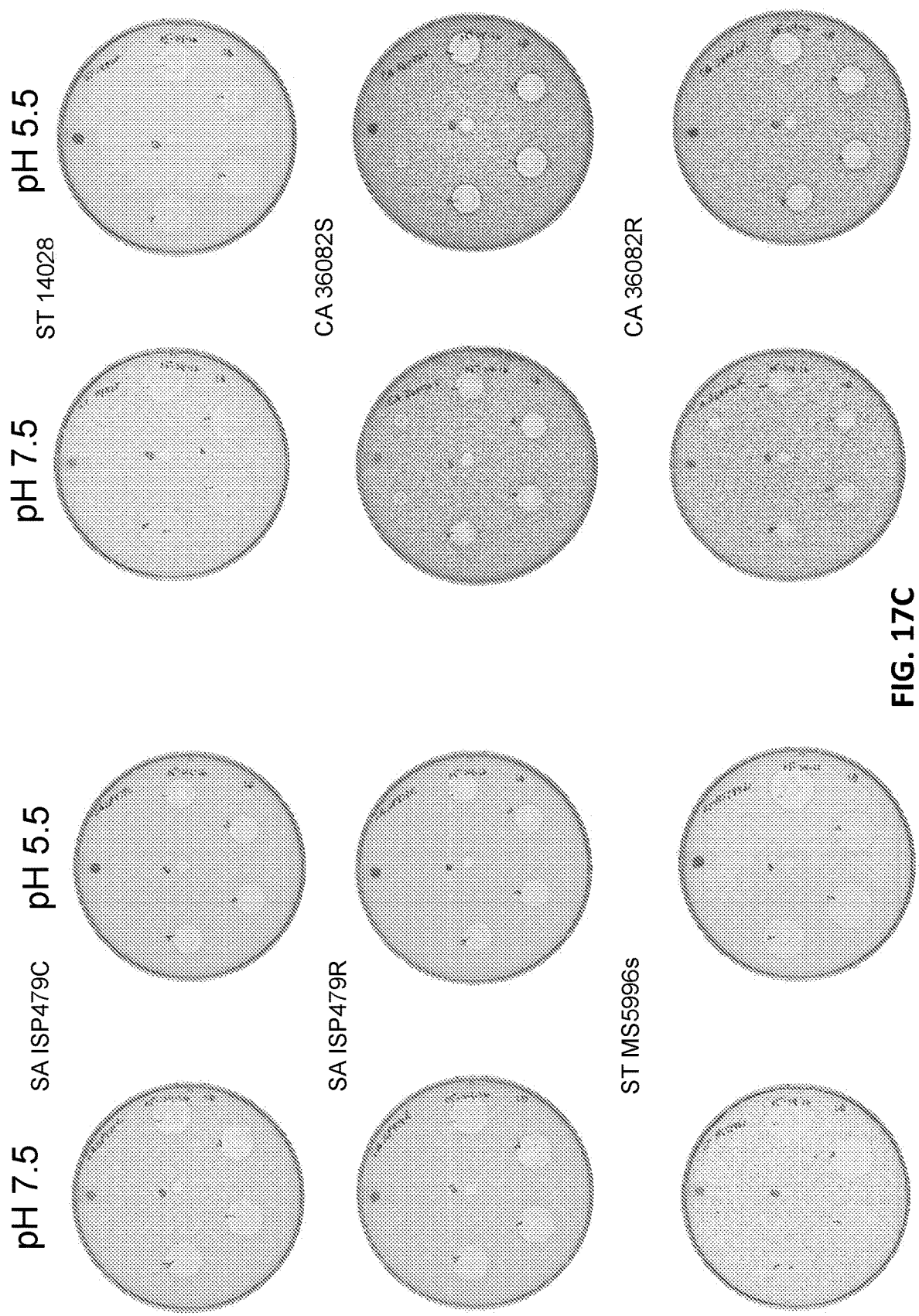

The testing results (at pH 5.5 and 7.5) are shown in FIG. 17A-C, which show that all of these variants were active against a spectrum of bacterial species.

Unless otherwise defined, all technical and scientific terms used herein have the same meaning as commonly understood by one of ordinary skill in the art to which this disclosure belongs.

The disclosures illustratively described herein may suitably be practiced in the absence of any element or elements, limitation or limitations, not specifically disclosed herein. Thus, for example, the terms "comprising", "including," "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the disclosure claimed.

Thus, it should be understood that although the present disclosure has been specifically disclosed by preferred embodiments and optional features, modification, improvement and variation of the disclosures embodied therein herein disclosed may be resorted to by those skilled in the art, and that such modifications, improvements and variations are considered to be within the scope of this disclosure.

The materials, methods, and examples provided here are representative of preferred embodiments, are exemplary, and are not intended as limitations on the scope of the disclosure.

The disclosure has been described broadly and generically herein. Each of the narrower species and subgeneric groupings falling within the generic disclosure also form part of the disclosure. This includes the generic description of the disclosure with a proviso or negative limitation removing any subject matter from the genus, regardless of whether or not the excised material is specifically recited herein.

In addition, where features or aspects of the disclosure are described in terms of Markush groups, those skilled in the art will recognize that the disclosure is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. An isolated peptide comprising the amino acid sequence of SEQ ID NO:1 (CPTAQLIATLKNGRKICLD-LQALYKKFKKKLLKSLKRLG).

2. An isolated peptide comprising the amino acid sequence of SEQ ID NO:14 (CPTAQLIATLKNGRKICLD-LQPALYKKFKKKLLKSLKRLG).

3. An isolated peptide comprising the amino acid sequence of SEQ ID NO:17 (CPTAQLIATLKNGPKICLD-LQALYKKFKKKLLKSLKRLG).

4. The isolated peptide of claim 1, wherein the peptide is not longer than 100 amino acids in length.

5. The isolated peptide of claim 1, wherein the peptide has antimicrobial activity.

6. A polynucleotide comprising a nucleic acid sequence encoding the peptide of claim 1.

7. A composition comprising the peptide of claim 1 and a pharmaceutically acceptable carrier.

8. The composition of claim 7, further comprising an antimicrobial agent.

9. The composition of claim 8, wherein the antimicrobial agent is selected from the group consisting of imipenem, ceftazidime, colistin, chloroquine, artemisinin, vancomycin and daptomycin.

10. A method of treating an infection in a patient in need thereof, comprising administering to the patient an effective amount of the peptide of claim 1.

11. The method of claim 10, wherein the infection is caused by multidrug-resistant *Pseudomonas aeruginosa* (MDRPA) or multidrug-resistant *Acinetobacter baumannii* (MDRAB).

12. The method of claim 11, wherein the patient suffers from a disease or condition selected from the group consisting of wound abscess, catheter biofilm, pneumonia, and bacteremia.

13. The method of claim 10, wherein the infection is caused by a parasite.

14. The method of claim 13, wherein the patient suffers from malaria.

15. The method of claim 10, wherein the administration is intravenous or topical.

16. A method of treating an infection in a patient in need thereof, comprising administering to the patient an effective amount of the peptide of claim 2.

17. The method of claim 16, wherein the infection is caused by multidrug-resistant *Pseudomonas aeruginosa* (MDRPA) or multidrug-resistant *Acinetobacter baumannii* (MDRAB).

18. The method of claim 16, wherein the infection is caused by a parasite.

19. A method of treating an infection in a patient in need thereof, comprising administering to the patient an effective amount of the peptide of claim 3.

20. The method of claim 19, wherein the infection is caused by multidrug-resistant *Pseudomonas aeruginosa* (MDRPA) or multidrug-resistant *Acinetobacter baumannii* (MDRAB).

* * * * *